US009324956B2

(12) United States Patent
Etori et al.

(10) Patent No.: US 9,324,956 B2
(45) Date of Patent: Apr. 26, 2016

(54) PHTHALOCYANINE NANO-SIZE STRUCTURES, AND ELECTRONIC ELEMENTS USING SAID NANO-SIZE STRUCTURES

(71) Applicant: DIC Corporation, Tokyo (JP)

(72) Inventors: Hideki Etori, Sakura (JP); Hideyuki Murata, Sakura (JP); Shou Inagaki, Sakura (JP); Engel Michael, Sakura (JP)

(73) Assignee: DIC Corporation, Tokyo (JP)

( * ) Notice: Subject to any disclaimer, the term of this patent is extended or adjusted under 35 U.S.C. 154(b) by 12 days.

(21) Appl. No.: 14/390,610

(22) PCT Filed: Apr. 4, 2013

(86) PCT No.: PCT/JP2013/060319
§ 371 (c)(1),
(2) Date: Oct. 3, 2014

(87) PCT Pub. No.: WO2013/151128
PCT Pub. Date: Oct. 10, 2013

(65) Prior Publication Data
US 2015/0090975 A1  Apr. 2, 2015

(30) Foreign Application Priority Data

Apr. 6, 2012 (JP) ................................ 2012-087388

(51) Int. Cl.
| H01L 51/00 | (2006.01) |
| B82Y 30/00 | (2011.01) |
| C07D 487/22 | (2006.01) |
| C09B 47/06 | (2006.01) |
| C09B 47/067 | (2006.01) |
| C09B 47/24 | (2006.01) |
| C09B 67/50 | (2006.01) |
| C09D 11/322 | (2014.01) |
| C09D 11/52 | (2014.01) |
| H01L 51/05 | (2006.01) |
| B82Y 40/00 | (2011.01) |
| H01L 51/42 | (2006.01) |

(52) U.S. Cl.
CPC ............. *H01L 51/0078* (2013.01); *B82Y 30/00* (2013.01); *C07D 487/22* (2013.01); *C09B 47/065* (2013.01); *C09B 47/0678* (2013.01); *C09B 47/24* (2013.01); *C09B 67/0026* (2013.01); *C09D 11/322* (2013.01); *C09D 11/52* (2013.01); *H01L 51/0003* (2013.01); *H01L 51/0007* (2013.01); *B82Y 40/00* (2013.01); *H01L 51/0545* (2013.01); *H01L 51/4206* (2013.01); *Y02E 10/549* (2013.01); *Y02P 70/521* (2015.11)

(58) Field of Classification Search
CPC ............ H01L 51/0078; H01L 51/0007; H01L 51/0003; C09B 47/065; C09B 47/0678; C09B 47/24; C09B 67/0026; C09D 11/322; C09D 11/52; C07D 487/22; B82Y 30/00
USPC ............. 252/500, 519.21; 257/40; 438/82, 99
See application file for complete search history.

(56) References Cited

U.S. PATENT DOCUMENTS

| 2004/0045478 A1 | 3/2004 | Tateishi et al. |
| 2004/0187232 A1 | 9/2004 | Chino et al. |
| 2006/0076298 A1 | 4/2006 | Nakanishi et al. |
| 2012/0104335 A1 | 5/2012 | Etori et al. |
| 2012/0308822 A1 | 12/2012 | Etori et al. |

FOREIGN PATENT DOCUMENTS

| EP | 1364994 A1 | 11/2003 |
| EP | 1437388 A1 | 7/2004 |
| JP | S61-104601 A | 5/1986 |
| JP | 2001-131453 A | 5/2001 |
| JP | 2002-121420 A | 4/2002 |
| JP | 2004-091560 A | 3/2004 |
| JP | 2008-303383 A | 12/2008 |
| JP | 2009-227692 A | 10/2009 |
| JP | 2009-280531 A | 12/2009 |
| WO | WO-2010/122921 A1 | 10/2010 |
| WO | WO-2011/065133 A1 | 6/2011 |

OTHER PUBLICATIONS

International Search Report mailed May 28, 2013, issued for PCT/JP2013/060319.
Christos D. Dimitrakopoulos et al., "Organic Thin Film Transistors for Large Area Electronics," Advanced Materials, vol. 14, No. 2, Jan. 16, 2002, pp. 99-117.
R. Zeis et al., "Single-crystal field-effect transistors based on copper phthalocyanine," Applied Physics Letters 86, 2005, pp. 022103-1 to 022103-3.
Supplementary European Search Report dated Dec. 7, 2015, issued for the European patent application No. 13772052.0.

*Primary Examiner* — Porfirio Nazario Gonzalez
(74) *Attorney, Agent, or Firm* — Locke Lord LLP

(57) ABSTRACT

There is provided an organic semiconductor material with which it is possible to manufacture an electronic element by a wet process which is low cost. Furthermore, the object is to provide an organic semiconductor electronic element which is hardly broken, light in weight and inexpensive, and has high characteristic. According to the present invention, it has been found that it is possible to provide an organic semiconductor material in which performance is improved and which is suitable for a wet process by optimizing a phthalocyanine derivative which configures a phthalocyanine nano-sized substance and the completion of the present invention has been reached. Furthermore, it is possible to provide an electronic element which has high durability, is hardly broken, light in weight, inexpensive and has high characteristic by using the organic semiconductor material in an electronic element active part (a semiconductor layer).

9 Claims, 6 Drawing Sheets

PHTHALOCYANINE NANO-SIZE STRUCTURES, AND ELECTRONIC ELEMENTS USING SAID NANO-SIZE STRUCTURES

TECHNICAL FIELD

The present invention relates to a phthalocyanine nano-sized substance, an ink composition containing the above phthalocyanine nano-sized substance, an electronic element containing the above phthalocyanine nano-sized substance, a transistor containing the above phthalocyanine nano-sized substance in a channel and a photoelectric conversion element containing the above phthalocyanine nano-sized substance between a positive electrode and a negative electrode.

BACKGROUND ART

"Information terminal which is hardly broken, light in weight and inexpensive" which any one can use at any place has been recently required. In order to realize this, the use of a material which has cost benefit and is soft is desired in a transistor which is a key device (the most important element) of information terminal. However, an inorganic material such as silicon which has been conventionally used can not sufficiently meet such demand.

Due to such a condition, "an organic transistor (OFET)" using an organic compound having semiconductor characteristics, which is called an organic semiconductor, in an active part (a semiconductor layer) of the transistor has been the focus of attention (refer to NPL 1). Such the organic semiconductor is soft and is capable of treating at low temperature, and an affinity for a solvent is generally high. Therefore, there is an advantage that the semiconductor layer can be manufactured (film-deposited) on a plastic substrate which is flexible by using a wet process such as coating or printing at a low cost, and the organic semiconductor is expected as a next-generation material for electronic element which is essential for a realization of "information terminal which is hardly broken, light in weight and inexpensive".

Phthalocyanines are one of the typical organic semiconductors, and it is known that excellent transistor characteristics are exhibited by controlling a higher-order structure, that is, an arrangement and an aggregation state of molecules (refer to NPL 2). However, since phthalocyanines have low solvent solubility, it is difficult to produce an element by the wet process, therefore, when phthalocyanines are used for an electronic element, a dry process such as vacuum evaporation or sputtering is generally used. Since such the dry process is a complicated and expensive process, it becomes difficult to provide a low cost electronic element which is one of characteristics of the organic semiconductor.

In order to solve the problem, a technology which manufactures a transistor by the wet process by introducing a solubilizing substituent into phthalocyanines and enhancing the solvent solubility, is also disclosed (refer to PTL 1). However, in the method, since each molecule of phthalocyanines is not sufficiently arranged and the higher-order structure can not be controlled, transistor characteristics are inferior, as compared with a transistor by a dry process. In order to exhibit excellent semiconductor characteristics, it is important that each molecule has a crystal structure having dimensionality in which each molecule arranges in a certain direction; therefore, there is an expectation in a wire- or rod-like one-dimensional crystalline structure (a crystalline structure having a major axis (a long axis) and a minor axis (a short axis)).

On the other hand, in order to more favorably apply them toward the electronic element in which the production by the wet process is expected, the above one-dimensional crystalline structure is a one-dimensional crystalline structure in which the minor axis is preferably 500 nm or less (hereinafter, written as a nano-sized one-dimensional substance).

Phthalocyanines are widely used as a coloring agent for paint in a printing ink, and many technologies which control the crystal size or the shape thereof are also known. For example, there are a solvent salt milling method of mixing an inorganic salt and an organic solvent with a metal phthalocyanine and finely grinding and micronizing pigments by using a grinding device (for example, refer to PTL 2), a crystallization method of settling out the above metal phthalocyanine in a large quantity of water after it is dissolved in sulfuric acid (for example, refer to PTL 3), and the like. However, even using these methods, it was difficult to obtain the nano-sized substance composed of phthalocyanines as described above.

On the other hand, the present inventors disclose a technology of manufacturing a device by a wet process using the phthalocyanine nanowire which is produced using unsubstituted phthalocyanine and phthalocyanine having a substituent (refer to PTLS 4, 5 and 6). However, it is difficult to say that the above phthalocyanine nanowire is completely optimized in a performance aspect.

CITATION LIST

Non Patent Literature

[NPL 1] Advanced Materials, 2002, Volume 14, Page 99
[NPL 2] Applied Physics Letters, 2005, Volume 86, Page 22103

PATENT LITERATURE

[PTL 1] Japanese Unexamined Patent Application, First Publication No. 2008-303383
[PTL 2] Japanese Unexamined Patent Application, First Publication No. 2002-121420
[PTL 3] Japanese Unexamined Patent Application, First Publication No. 2004-091560
[PTL 4] Japanese Unexamined Patent Application, First Publication No. 2009-280531
[PTL 5] WO2010/122921
[PTL 6] WO2011/065133

SUMMARY OF INVENTION

Technical Problem

The present invention has been made in view of the above problem, and can provide an organic semiconductor material with which it is possible to manufacture an electronic element by a wet process which is low cost. Furthermore, an organic semiconductor electronic element which is hardly broken, light in weight and inexpensive, and has high characteristics can be provided.

Solution to Problem

In order to achieve the object described above, the present inventors found that it was possible to provide an organic semiconductor material in which performance was improved and which was suitable for a wet process by optimizing a phthalocyanine derivative which configures a phthalocyanine nano-sized substance and have reached the completion of the present invention, as a result of intensive studies. Furthermore, it was found that it was possible to provide an electronic element which had high durability, was hardly broken, light in weight, inexpensive and had high characteristics by using the above organic semiconductor material in an electronic element active part (a semiconductor layer), and the completion of the present invention has been reached.

That is, the present invention is to provide a phthalocyanine nano-sized substance containing unsubstituted phthalocyanine and phthalocyanine having a substituent, in which a shape of the substance has a major axis and a minor axis, the minor axis is 500 nm or less, the unsubstituted phthalocyanine is represented by general formula (1) or (2):

[Chem. 1]

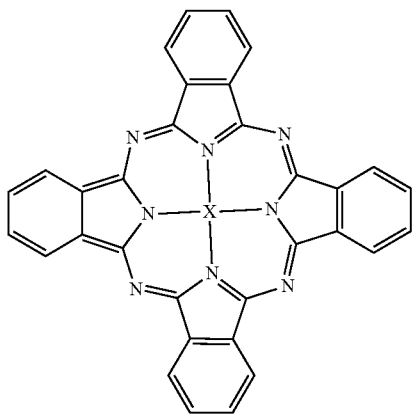

(1)

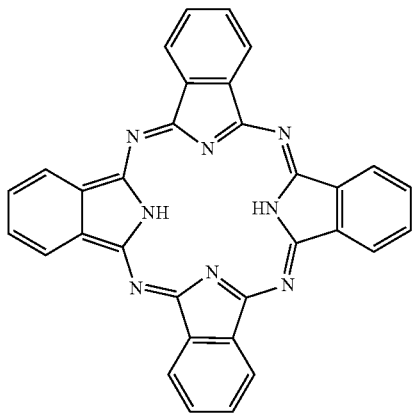

(2)

(provided that, in the formulae, X is any one selected from the group composed of a copper atom, a zinc atom, a cobalt atom, a nickel atom, a tin atom, a lead atom, a magnesium atom, an iron atom, a palladium atom, a calcium atom, GeO, TiO, VO and AlCl), and the phthalocyanine having a substituent is represented by general formula (3) or (4):

[Chem. 2]

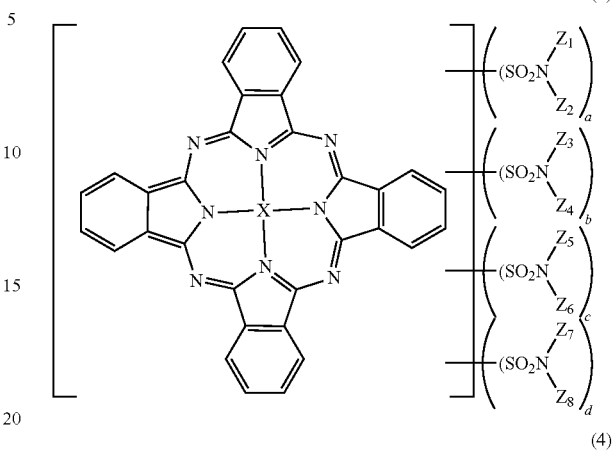

(3)

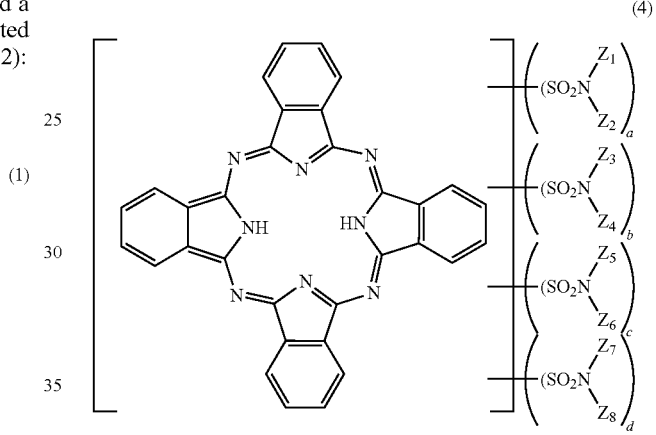

(4)

(provided that, in the formulae, X is any one selected from the group composed of a copper atom, a zinc atom, a cobalt atom, a nickel atom, a tin atom, a lead atom, a magnesium atom, an iron atom, a palladium atom, a calcium atom, GeO, TiO, VO and AlCl, each hydrogen atom in a benzene ring of a phthalocyanine skeleton may be substituted with fluorine, chlorine, bromine, $Z_1$ to $Z_8$ are each independently a hydrogen atom, an acyclic hydrocarbon group having 1 to 30 carbon atoms which may have a substituent, a cyclic hydrocarbon group having 1 to 30 carbon atoms which may have a substituent and a heteroaryl group which may have a substituent, a, b, c and d each independently represent an integer of 0 to 4, but, at least one of those is not 0, and a case where $Z_1$ to $Z_8$ are general formula (5) or (6) and a case where all of them are hydrogen atoms are excluded.)

[Chem. 3]

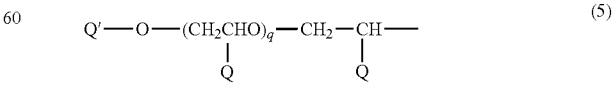

(5)

(Here, q is an integer of 4 to 100, Q is each independently a hydrogen atom or a methyl group, and Q' is an acyclic hydrocarbon group having 1 to 30 carbon atoms.)

[Chem. 4]

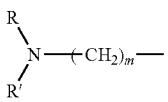
(6)

(Here, m is an integer of 1 to 20, R and R' are each independently an alkyl group having 1 to 20 carbon atoms.)

Advantageous Effects of Invention

According to the present invention, since the phthalocyanine nano-sized substance according to the present invention consists of phthalocyanines having high durability, it is possible to provide the electronic element with a long life. In addition, since the phthalocyanine nano-sized substance according to the present invention is superior in dispersibility to solvent to well-known phthalocyanine pigment fine particles, it becomes easier to form an ink composition; therefore, it becomes possible to form a semiconductor layer on a flexible plastic substrate or the like by a printing method, and thus it is possible to provide the electronic element which is hardly broken, light in weight and inexpensive. Furthermore, since the arrangement controllability of a phthalocyanine molecule over the whole substance in the phthalocyanine nano-sized substance according to the present invention is higher than that of well-known phthalocyanine pigment fine particles, an improvement of semiconductor characteristics can be achieved. In addition, since a phthalocyanine derivative which configures a nano-sized substance in the phthalocyanine nano-sized substance according to the present invention is optimized more than the phthalocyanine nano-sized substances (the nanowires) described in [PTL 4], [PTL 5] and [PTL 6], semiconductor characteristics are improved, and as a result, it is possible to provide the electronic element in which the charge mobility (hereinafter, simply written as the mobility) has been improved.

DESCRIPTION OF EMBODIMENTS

<Phthalocyanine Nano-sized Substance>

Figure 1:
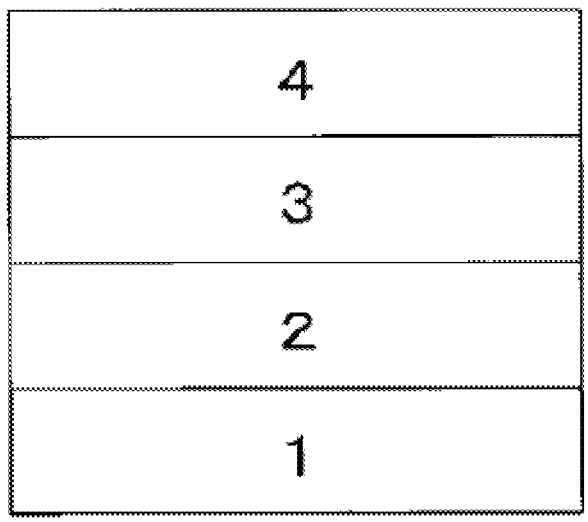
FIG. 1 is a schematic cross-section of a photoelectric conversion element according to the present invention.

Hereinafter, description will be given of a phthalocyanine nano-sized substance of the present invention.

The phthalocyanine nano-sized substance of the present invention is one-dimensional (linear such as wire-like, fiber-like, string-like, needle-like, rod-like) structure having a major axis (a long axis) and a minor axis (a short axis), the minor axis is 500 nm or less, more preferably 300 nm or less and most preferably 100 nm or less, and unsubstituted phthalocyanine and phthalocyanine having a substituent (a phthalocyanine derivative) are included as a constituent material for substance. Here, as to the major axis, if (the major axis/the minor axis)>1 (the major axis/the minor axis is bigger than 1), there is no particular limitation. In addition, as to the mixture ratio of unsubstituted phthalocyanine and phthalocyanine having a substituent, the mixture ratio of phthalocyanine having a substituent to unsubstituted phthalocyanine ([the mass of phthalocyanine having a substituent×100]/[the mass of unsubstituted phthalocyanine]) is preferably in a range from 1% by mass to 200% by mass, and further preferably from 1% by mass to 120% by mass (described later).

As unsubstituted phthalocyanine which configures the phthalocyanine nano-sized substance of the present invention, phthalocyanine represented by general formula (1) and metal-free phthalocyanine represented by the formula (2) can be included.

[Chem. 5]

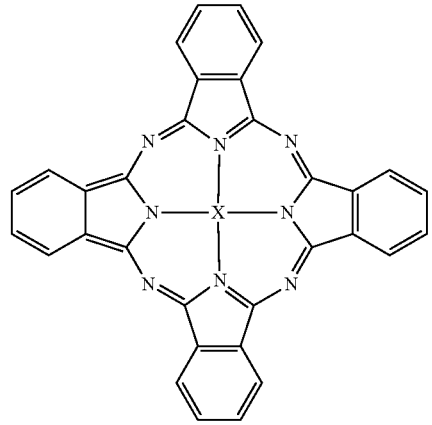
(1)

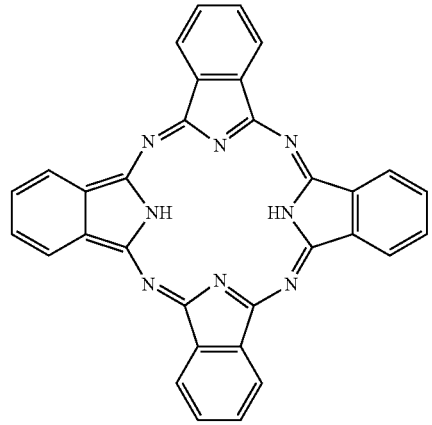
(2)

In general formula (1), there is no particular limitation of X as long as X is one which configures phthalocyanine, and, a metal atom such as a copper atom, a zinc atom, a cobalt atom, a nickel atom, a tin atom, a lead atom, a magnesium atom, an iron atom, a palladium atom or a calcium atom, and a metal oxide or a metal halide such as GeO, TiO (titanyl), VO (vanadyl) or AlCl (aluminum chloride) are included. Among those, a copper atom, a zinc atom and an iron atom are particularly preferable.

The characteristics of the phthalocyanine nano-sized substance of the present invention are to use, as phthalocyanine having a substituent, a phthalocyanine derivative represented by the following general formula (3) or (4) in which a hydrogen atom of a phthalocyanine skeleton is substituted with a sulfamoyl group (—$SO_2NZZ'$), which is called sulfamoyl group substituted phthalocyanine.

[Chem. 6]

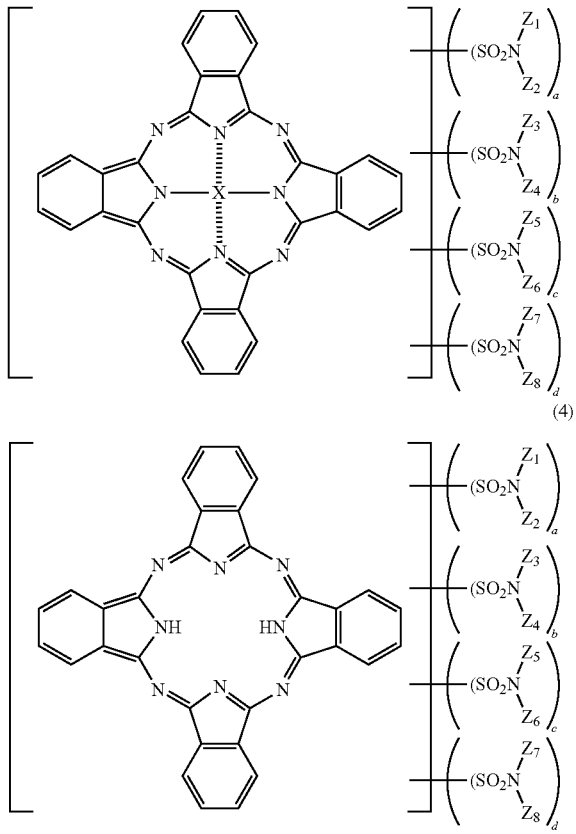

Provided that, in general formula (3) or (4), X in the formulae is any one selected from the group composed of a copper atom, a zinc atom, a cobalt atom, a nickel atom, a tin atom, a lead atom, a magnesium ion, an iron atom, a palladium atom, a calcium atom, GeO, TiO, VO and AlCl, each hydrogen atom in a benzene ring of the phthalocyanine skeleton may be substituted with fluorine, chlorine or bromine, $Z_1$ to $Z_8$ are each independently a hydrogen atom, an acyclic hydrocarbon group having 1 to 30 carbon atoms which may have a substituent, a cyclic hydrocarbon group having 1 to 30 carbon atoms which may have a substituent or a heteroaryl group which may have a substituent, a, b, c and d represent each independently an integer of 0 to 4, but, at least one of those is not 0, and a case where $Z_1$ to $Z_8$ are general formula (5) or (6) and a case where all of them are hydrogen atoms are excluded.

[Chem. 7]

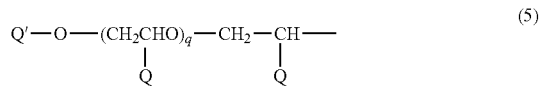

(Here, q is an integer of 4 to 100, Q is each independently a hydrogen atom or a methyl group, and Q' is an acyclic hydrocarbon group having 1 to 30 carbon atoms.)

[Chem. 8]

(Here, m is an integer of 1 to 20, R and R' are each independently an alkyl group having 1 to 20 carbon atoms.)

The above-mentioned acyclic hydrocarbon group having 1 to 30 carbon atoms which may have a substituent may be either a linear hydrocarbon group or a branched hydrocarbon group, and the hydrocarbon group may be either a saturated hydrocarbon group or an unsaturated hydrocarbon group. As such the acyclic hydrocarbon group, for example, a linear or branched saturated hydrocarbon group such as a methyl group, an ethyl group, an n-propyl group, an isopropyl group, an n-butyl group, an isobutyl group, a sec-butyl group, a tert-butyl group, a 1-pentyl group, a 2-pentyl group, a 3-pentyl group, a 1-(2-metyl)-butyl group, a 2-(2-metyl)-butyl group, a 1-(3-metyl)-butyl group, a 2-(3-metyl)-butyl group, a (2,2-dimethyl)-propyl group (another name: a neopentyl group), a hexyl group, an n-hexyl group, a heptyl group, an n-heptyl group, an octyl group, an n-octyl group, 2-ethylhexyl group, a nonyl group, a decyl group, an n-decyl group, an undecyl group, a dodecyl group, an n-dodecyl group, a tridecyl group, an n-tridecyl group, a tetradecyl group, an n-tetradecyl group, a pentadecyl group, an n-pentadecyl group, a hexadecyl group, an n-hexadecyl group, a heptadecyl group, an n-heptadecyl group, an octadecyl group, a stearyl group (an n-octadecyl group), a nonadecyl group, an n-nonadecyl group, an n-tetracosyl group or an n-triacontyl group can be included, and an arbitrary hydrogen atom in the hydrocarbon group may be substituted with a well-known substituent (described later) capable of being substituted in a hydrocarbon group. Among those, one having 25 or less carbon atoms is preferable, and one having 22 or less carbon atoms is further preferable, from the viewpoint of semiconductor characteristics.

In addition, for example, a linear or branched unsaturated hydrocarbon group such as a vinyl group, a 1-propenyl group, an allyl group, an isopropenyl group, a butenyl group, a pentenyl group, an isoprene group, a hexenyl group, a heptenyl group, an octenyl group, a decenyl group, a geranyl group, an ethynyl group or 2-propynyl group can be included, and an arbitrary hydrogen atom in the hydrocarbon group may be substituted with a well-known substituent (described later) capable of being substituted in a hydrocarbon group. Among those, one having 25 or less carbon atoms is preferable, and one having 22 or less carbon atoms is further preferable, from the viewpoint of semiconductor characteristics.

As a specific example of the well-known substituent capable of being substituted in the acyclic hydrocarbon group having 1 to 30 carbon atoms described above, —F, —Cl, —Br, an alkoxy group, a thioalkoxy group, an amino group, —SO$_2$NHY$^1$ (Y$^1$ represents an alkyl group which may have a substituent), —COOY$^2$ (Y$^2$ represents an alkyl group which may have a substituent), —N$_3$, —CN, —NC, —NO$_2$, —NY$^3_3$$^+$A$^-$ (Y$^3$ represents hydrogen or an alkyl group which may have a substituent and A$^-$ represents a monovalent anionic species), —OH, —O$^-$L$^+$ (L$^+$ represents a monovalent cationic species such as Li$^+$, Na$^+$, K$^+$ or an ammonium salt), —SH, —S$^-$L$^+$ (L$^+$ represents a monovalent cationic species such as Li$^+$, Na$^+$, K$^+$ or an ammonium salt), —SO$_2$H, —SO$_2^-$L$^+$ (L$^+$ represents a monovalent cationic species such as Li$^+$, Na$^+$, K$^+$ or an ammonium salt), —SO$_3$H, —SO$_3^-$L$^+$ (L$^+$ represents a monovalent cationic species such as Li$^+$, Na$^+$, K$^+$ or an ammonium salt), —CHO, —COOH, —COO$^-$L$^+$ (L$^+$ represents a monovalent cationic species such as Li$^+$, Na$^+$, K$^+$ or an ammonium salt), —B(OY$^4$)$_3$ (Y$^4$ represents hydrogen or an alkyl group which may have a substituent), —SiY$^5_3$ (Y$^5$ represents hydrogen or an alkyl group which may have a substituent), —Si(OY$^6$)$_3$ (Y$^6$ represents hydrogen or an alkyl group which may have a substituent), —P(=O)(OY$^7$)$_2$ (Y$^7$ represents hydrogen or an alkyl group which may have a substituent), —CONY$^9$Y$^{10}$ (Y$^9$ and Y$^{10}$ each independently represent hydrogen or an alkyl group which may have a substituent), and the like can be included, and —F, —Cl, an amino group, a hydroxyl group, —P(=O)(OH)$_2$, —SO$_2$NHY$^1$ (Y$^1$ represents an alkyl group which may have a substituent) and an alkoxy group are preferable.

As a cyclic hydrocarbon group having 1 to 30 carbon atoms which may have a substituent, a cyclopentyl group, a cyclohexyl group, a phenyl group, a naphthyl group, and the like can be included, and an arbitrary hydrogen atom in the cyclic hydrocarbon group may be substituted with a well-known substituent (described later) capable of being substituted in a cyclic hydrocarbon group.

As a specific example of the well-known substituent capable of being substituted in the cyclic hydrocarbon group described above, —F, —Cl, —Br, an alkoxy group, a thioalkoxy group, an amino group, —SO$_2$NHY$^1$ (Y$^1$ represents an alkyl group which may have a substituent), —COOY$^2$ (Y$^2$ represents an alkyl group which may have a substituent), —N$_3$, —CN, —NC, —NO$_2$, —NY$^3_3$$^+$ A$^-$ (Y$^3$ represents hydrogen or an alkyl group which may have a substituent and A$^-$ represents a monovalent anionic species), —OH, —O$^-$L$^+$ (L$^+$ represents a monovalent cationic species such as Li$^+$, Na$^+$, K$^+$ or an ammonium salt), —SH, —S$^-$L$^+$ (L$^+$ represents a monovalent cationic species such as Li$^+$, Na$^+$, K$^+$ or an ammonium salt), —SO$_2$H, —SO$_2^-$L$^+$ (L$^+$ represents a monovalent cationic species such as Li$^+$, Na$^+$, K$^+$ or an ammonium salt), —SO$_3$H, —SO$_3^-$L$^+$ (L$^+$ represents a monovalent cationic species such as Li$^+$, Na$^+$, K$^+$ or an ammonium salt), —CHO, —COOH, —COO$^-$L$^+$ (L$^+$ represents a monovalent cationic species such as Li$^+$, Na$^+$, K$^+$ or an ammonium salt), —B(OY$^4$)$_3$ (Y$^4$ represents hydrogen or an alkyl group which may have a substituent), —SiY$^5_3$ (Y$^5$ represents hydrogen or an alkyl group which may have a substituent), —Si(OY$^6$)$_3$ (Y$^6$ represents hydrogen or an alkyl group which may have a substituent), —P(=O)(OY$^7$)$_2$ (Y$^7$ represents hydrogen or an alkyl group which may have a substituent), and —CONY$^9$Y$^{10}$ (Y$^9$ and Y$^{10}$ each independently represent hydrogen or an alkyl group which may have a substituent), an alkyl group, a aryl group, a heteroaryl group, —N=N—Y$^8$ (Y$^8$ represents an alkyl group which may have a substituent or an aryl group which may have a substituent), and the like can be included, and —F, —Cl, —CN, an amino group, a hydroxyl group, —P(=O)(OH)$_2$, —SO$_2$NHY$^1$ (Y$^1$ represents an alkyl group which may have a substituent), an alkoxy group, alkyl group and an aryl group are preferable.

As the heteroaryl group described above which may have a substituent, a pyrrolyl group, a thienyl group (a 2-thienyl group and a 3-thienyl group), a pyrazolyl group, a thiazolyl group, a benzothiazolyl group, a benzoisothiazolyl group, an imidazolyl group, and a benzotriazolyl group can be included, and as a substituent, a well-known substituent (described later) capable of being substituted in the heteroaryl group can be included.

As a specific example of the general well-known substituent capable of being substituted in the heteroaryl group described above, —F, —Cl, —Br, an alkoxy group, a thioalkoxy group, an amino group, —SO$_2$NHY$^1$ (Y$^1$ represents an alkyl group which may have a substituent), —COOY$^2$ (Y$^2$ represents an alkyl group which may have a substituent), —N$_3$, —CN, —NC, —NO$_2$, —NY$^3_3$$^+$A$^-$ (Y$^3$ represents hydrogen or an alkyl group which may have a substituent and A$^-$ represents a monovalent anionic species), —OH, —O$^-$L$^+$ (L$^+$ represents a monovalent cationic species such as Li$^+$, Na$^+$, K$^+$ or an ammonium salt), —SH, —S$^-$L$^+$ (L$^+$ represents a monovalent cationic species such as Li$^+$, Na$^+$, K$^+$ or an ammonium salt), —SO$_2$H, —SO$_2^-$L$^+$ (L$^+$ represents a monovalent cationic species such as Li$^+$, Na$^+$, K$^+$ or an ammonium salt), —SO$_3$H, —SO$_3^-$L$^+$ (L$^+$ represents a monovalent cationic species such as Li$^+$, Na$^+$, K$^+$ or an ammonium salt), —CHO, —COOH, —COO$^-$L$^4$ (L represents a monovalent cationic species such as Li$^+$, Na$^+$, K$^+$ or an ammonium salt), —B(OY$^4$)$_3$ (Y$^4$ represents hydrogen or an alkyl group which may have a substituent), —SiY$^5_3$ (Y$^5$ represents hydrogen or an alkyl group which may have a substituent), —Si(OY$^6$)$_3$ (Y$^6$ represents hydrogen or an alkyl group which may have a substituent), —F(=O)(OY$^7$)$_2$ (Y$^7$ represents hydrogen or an alkyl group which may have a substituent), and —CONY$^9$Y$^{10}$ (Y$^9$ and Y$^{10}$ each independently represent hydrogen or an alkyl group which may have a substituent), an alkyl group, a aryl group, a heteroaryl group, —N=N—Y$^8$ (Y$^8$ represents an alkyl group which may have a substituent or an aryl group which may have a substituent), and the like can be included, and —F, —Cl, —CN, an amino group, a hydroxyl group, —P(=O)(OH)$_2$, —SO$_2$NHY$^1$ (Y$^1$ represents an alkyl group which may have a substituent), an alkoxy group, an alkyl group and an aryl group are preferable.

Phthalocyanine having a substituent, which is represented by general formula (3) or (4), is a compound in which at least one hydrogen or more in the phthalocyanine skeleton is substituted with a sulfamoyl group (—SO$_2$NZZ') (sulfamoyl group substituted phthalocyanine). a, b, c and d in general formula (3) or (4) represent the number of introduced substituents of the above sulfamoyl group, each independently represent an integer of 0 to 4, and, at least one of those is not 0. That is, the sulfamoyl group which is introduced may be at least one, is preferably 4 or less, further preferably 2 or less, and most preferably 1. Moreover, the substituted position is not particularly limited.

Specific examples of the substituent (a sulfamoyl group: —SO$_2$NZZ') of phthalocyanine having a substituent, which is represented by general formula (3) or (4), are shown below, and, a substituent of phthalocyanine having a substituent used in the phthalocyanine nano-sized substance of the present invention is not limited thereto.

—SO$_2$NH—CH$_3$
—SO$_2$NH—CH$_2$CH$_3$
—SO$_2$NH—CH$_2$CH$_2$CH$_3$
—SO$_2$NH—CH(CH$_3$)$_2$
—SO$_2$NH—CH$_2$CH$_2$CH$_2$CH$_3$
—SO$_2$NH—CH(CH$_3$)(CH$_2$CH$_3$)
—SO$_2$NH—CH$_2$—CH(CH$_3$)$_2$
—SO$_2$NH—C(CH$_3$)$_3$
—SO$_2$NH—(CH$_2$)$_4$CH$_3$
—SO$_2$NH—(CH$_2$)$_5$CH$_3$
—SO$_2$NH—(CH$_2$)$_7$CH$_3$
—SO$_2$NH—(CH$_2$)$_{11}$CH$_3$
—SO$_2$NH—(CH$_2$)$_{17}$CH$_3$
—SO$_2$NH—(CH$_2$)$_{21}$CH$_3$
—SO$_2$NH—Cy (Cy represents a cyclohexyl group.)

—SO$_2$NH-Ph
—SO$_2$NH—Th (Th represents a thienyl group.)

—SO$_2$N(CH$_3$)$_2$
—SO$_2$N(CH$_2$CH$_3$)$_2$

[Chem. 9]

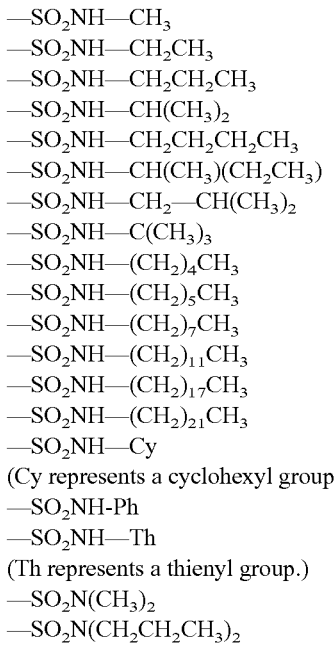

(7)

(8)

(9)

(10)

(11)

(12)

Phthalocyanine having a substituent, which is represented by general formula (3) or (4), can be obtained by combining well-known, common methods. For example, copper phthalocyanine sulfonyl chloride has to be reacted with an amine represented by the following formula [Chem. 10].

[Chem. 10]

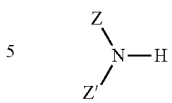

Copper phthalocyanine sulfonyl chloride which is used as a starting material can be obtained by a reaction of copper phthalocyanine with chlorosulfuric acid or thionyl chloride. Amine which is another starting material and represented by [Chem. 10] can be obtained by well-known, common methods. For example, it is possible to obtain by reductively aminating a hydroxyl group of alcohol using a nickel/copper/chromium catalyst and it is possible to obtain by imidizing the above hydroxyl group by the Mitsunobu reaction (reference literature: Synthesis, 1981, p. 1), afterward, aminating by the hydrazine reduction (reference literature: Chemical Communications, 2003, P. 2062). In addition, many amines have been provided as a commercial product.

<Method of Manufacturing Phthalocyanine Nano-Sized Substance>

As a method of manufacturing the phthalocyanine nano-sized substance of the present invention, for example, the methods described in WO2010/122921, Japanese Unexamined Patent Application, First Publication No. 2009-280531 and WO2011/065133 can be used. In addition, a method of decreasing the aspect ratio of the nano-sized substance by adjusting the ratio of the major axis/the minor axis (the aspect ratio) of the nano-sized substance obtained by the methods described in these publications can be also used as a method of manufacturing the phthalocyanine nano-sized substance of the present invention. Hereinafter, specific examples will be shown.

As an example of the method of manufacturing the phthalocyanine nano-sized substance of the present invention, a method is exemplified in which (a) a step (a) of obtaining a complex by precipitation into a poor solvent after dissolving unsubstituted phthalocyanine described above and phthalocyanine having a substituent described above in a good solvent, (b) a step (b) of obtaining a size-reduced complex by size-reducing the complex described above, and (c) a step (c) of making the size-reduced complex described above into a nano-sized one-dimensional substance (nanowire, or nanorod) by one-dimensionally growing a crystal (crystal growth in one direction) in an organic solvent, are included.

(Step (a))

It is generally known that phthalocyanines are soluble in an acid solvent such as sulfuric acid, and in the method of manufacturing the phthalocyanine nano-sized substance of the present invention, firstly, unsubstituted phthalocyanine described above and phthalocyanine having a substituent described above (sulfamoyl group substituted phthalocyanine) are dissolved in an acid solvent such as sulfuric acid, chlorosulfuric acid, methanesulfonic acid or trifluoroacetic acid. Afterward, a complex of the above unsubstituted phthalocyanine and the above phthalocyanine having a substituent is precipitated by pouring the solution into a poor solvent such as water.

Here, the mixture ratio of the above phthalocyanine having a substituent (sulfamoyl group substituted phthalocyanine) to the above unsubstituted phthalocyanine is preferably in a range from 1% by mass to 200% by mass, and further preferably from 1% by mass to 120% by mass. In a case where the mixture ratio is 1% by mass or more, a crystal is grown in one

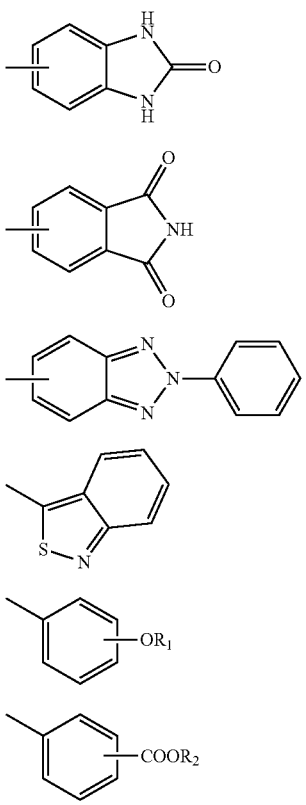

direction through a step described later to favorably make a one-dimensional structure, by an effect of a substituent of the above phthalocyanine having the substituent, on the other hand, if in a range of 200% by mass or less, since the number of the above functional group is not large enough to inhibit the crystal growth, the one-dimensional structure is made after favorably growing a crystal in one direction, and thus an amorphous state or an isotropic structure does not occur.

The dosage amount of the above unsubstituted phthalocyanine and the above phthalocyanine having a substituent to an acid solvent is not particularly limited as long as a concentration is obtained at which there is no undissolved portion and complete dissolution is achieved, and further, 20% by mass or less is preferable as a range which maintains a degree of viscosity with which the above solution has sufficient fluidity.

When the solution in which the above unsubstituted phthalocyanine and the above phthalocyanine having a substituent are dissolved is put into a poor solvent such as water to precipitate a complex of the above unsubstituted phthalocyanine and the above phthalocyanine having a substituent, the above solution is preferably in a range from 0.01% by mass to 50% by mass, with respect to a poor solvent. If 0.01% by mass or more, since the concentration of the above complex which is precipitated is sufficiently high, it is easy to collect the solid content, and if 50% by mass or less, since all of the above unsubstituted phthalocyanine and the above phthalocyanine having a substituent are precipitated to become the complex in a solid state, there is no soluble component and thus it becomes easier to collect the solid content.

The poor solvent described above is not particularly limited as long as it is a liquid in which unsubstituted phthalocyanine and phthalocyanine having a substituent are an insoluble or sparingly soluble;, water or an aqueous solution mainly composed of water, in which the homogeneity of the complex which is precipitated can be highly maintained, which is suitable for a step of size reduction described later, and the environmental burden of which is low, can be included as the most preferred poor solvent.

By removing the acid water by filtrating the above complex using filter paper and a Buchner funnel followed by washing with water until a filtrate becomes neutral, the above complex containing water can be collected. As to the collected complex, water is removed by dehydrating and drying, or in a next step (b), in a case of size-reducing by the wet process using a dispersion solvent having an affinity for water, a state containing water is sufficient as it is.

In the complex of unsubstituted phthalocyanine and phthalocyanine having a substituent obtained in the present step (a), it was confirmed that there was no crystal grain boundary and the complex was isotropic shaped structure, from the observation results using a transmission electron microscope.

(Step (b))

As to the step (b), a method thereof is not particularly limited as long as the complex which is obtained through the step (a) described above can be size-reduced. In a method of size-reducing the complex, there are the wet process (a method of performing the size-reduction in a dispersion solvent) and the dry process, and, in consideration of making the one-dimensional nano-sized substance by growing a crystal, using the size-reduced complex, in one direction in a solvent in the step (c), it is preferred that the complex described above be size-reduced using the wet process.

As a wet process, a method of treating the complex obtained in the step (a) with the dispersion solvent by using a media disperser using fine beads such as bead mills or a paint conditioner, a method of treating by using an emulsifying disperser typified by T.K. fill mix manufactured by PRIMIX Corporation, a method of treating by using a jet mill typified by a nanomizer manufactured by YOSHIDA KIKAI CO., LTD., and the like can be included. In addition, a treatment by irradiating with ultrasonic waves having a high output by using an ultrasonic homogenizer can be also applied, and these methods can be performed as one kind or as a combination of a plurality of kinds.

Here, as the dispersion solvent described above used in the wet process, water, an organic solvent, water-containing organic solvent and the like can be included. As an organic solvent, in addition to organic solvents (described later) used in the step (C) described later, alcohols such as ethanol, glycols, glycol esters can be included, and it is possible to perform the wet process by using these dispersion solvents either as one kind or as a combination of a plurality of kinds, and, water, ethanol, methanol, chlorobenzene, dichlorobenzene, N-methyl-2-pyrrolidone and propylene glycol monomethyl ester acetate are preferable, in terms of the suppression of the crystal growth and the crystal transition.

When the size-reduction is performed by the wet process, there is no particular limitation as to the mass ratio to the dispersion solvent of the above complex; and, it is preferred to treat in a range in which the solid content concentration is from 1% by mass to 30% by mass, from the viewpoint of the dispersion efficiency. In a case where fine media such as zirconia beads are used in the above treatment, the bead size thereof is preferably in a range from 0.01 mm to 2 mm, in consideration of a degree of the dispersion of the above complex. In addition, the used amount of fine media is most suitably in a range from 100% by mass to 1,000% by mass, with respect to the dispersion liquid of the above complex, from the viewpoint of the efficiency of size-reduction and the recovery efficiency.

Moreover, in a case where the size-reduction is conducted in water, water in an aqueous dispersion liquid of the obtained size-reduced complex is preferably removed by dehydrating and drying. A method of dehydrating and drying is not particularly limited; and, filtration, centrifugation, evaporation by a rotary evaporator or the like can be included. After dehydrating, drying may be performed until the water is completely removed by further using a vacuum dryer or the like.

In the present step (b), as to a degree of the size-reduction, the particle diameter of the complex obtained in the step (a) preferably becomes less than 1 μm, and from the viewpoint of promoting the size-reduced complex to be made into the one-dimensional structure with a nano-size by growing a crystal in one direction in the step (c) described later, the particle diameter preferably becomes less than 500 nm, and further preferably becomes less than 300 nm (the particle diameter is measured by dynamic light scattering).

(Step (c))

The step (c) is a step of making a nano-sized one-dimensional structure by growing a crystal in one direction (one-dimensional crystal growth) as to the size-reduced complex which is obtained through the step (b) described above. As to a degree of making the nano-sized one-dimensional structure, as the shape of the obtained nano-sized one-dimensional structure, the width (the minor axis) is preferably 500 nm or less, more preferably 300 nm or less, and most preferably 100 nm or less. As to a method of making the nano-sized one-dimensional structure, the method is not particularly limited as long as it is possible to make the above size-reduced complex into the nano-sized one-dimensional structure, and, a method of making the above size-reduced complex into the nano-sized one-dimensional structure in an organic solvent (in a liquid phase) can be included. Specifically, by stirring or leaving to stand the above size-reduced complex in an organic solvent (in a liquid phase), it is possible to make the above complex into the nano-sized one-dimensional structure. Moreover, when stirring or leaving to stand, it is preferred to perform in a state which is controlled under a predetermined temperature, from the viewpoint of controlling the shape of the nano-sized one-dimensional structure.

In a case of making the above size-reduced complex into the nano-sized one-dimensional structure in an organic solvent (in a liquid phase), the solvent which is used is not particularly limited as long as the solvent is not one having low affinity for phthalocyanines, and, for example, an amide-based organic solvent, an aromatic-based organic solvent, a halogen-based organic solvent, a glycol ester-based solvent, a glycol ether-based solvent, and the like having high affinity for phthalocyanines are preferable, and specifically, as an amide-based solvent, N,N-dimethylacetamide, N,N-dimethylformamide and N-methylpyrrolidone, as an aromatic-based organic solvent, toluene, xylene and ethylbenzene, as a halogen-based organic solvent, chlorobenzene, dichlorobenzene, chloroform, methylene chloride and dichloroethane, as a glycol ester-based solvent, ethylene glycol monomethyl ether acetate, diethylene glycol monoethyl ether acetate, diethylene glycol monobutyl ether acetate and propylene glycol monomethyl ether acetate, and as a glycol ether-based solvent, ethylene glycol methyl ether, ethylene glycol ethyl ether, ethylene glycol butyl ether, diethylene glycol ethyl ether, diethylene glycol butyl ether, propylene glycol monomethyl ether, propylene glycol monoethyl ether, propylene glycol monopropyl ether, propylene glycol tertiary butyl ether, dipropylene glycol monomethyl ether can be included as the most suitable organic solvent. The organic solvent described above can be used alone, can be used by combining at an arbitrary ratio, and can be used by further using other solvents together.

With regard to the dosage amount of the organic solvent to the above size-reduced complex, from the viewpoint of having appropriate fluidity and the prevention of the aggregation, the solid content concentration of the above complex to the above organic solvent is preferably in a range from 0.1% to 20%, and further preferably in a range from 1% to 10%.

The temperature of stirring or leaving to stand in a case of making the above complex into the nano-sized one-dimensional structure is preferably in a range from 5° C. to 300° C., and further preferably from 20° C. to 250° C. If the temperature is 5° C. or more, it is possible to sufficiently induce the crystal growth of phthalocyanines and thus it is possible for phthalocyanines to grow to the one-dimensional structure, due to the intended one-dimensional crystal growth, and if 250° C. or less, the aggregation and coalescence of generated one-dimensional structure are hardly found and further, coarsening by growing a crystal in a minor axis (width) direction (forming an isotropic structure) does not occur.

The time of stirring or the time of leaving to stand for making the one-dimensional structure is not particularly limited, and, it is preferred to perform stirring or leaving to stand at least for 10 minutes or more until the length of the nano-sized one-dimensional structure is grown to 100 nm or more.

Here, the solvent used in the present step (c) may be different from the solvent used in the wet size-reduction treatment in the step (b) described above. In that case, after the step (b) is conducted, the solvent used in the wet size-reduction treatment is removed and the size-reduced complex obtained in this manner is re-dispersed in a solvent used in the present step (c). A method of removing the solvent used in the step (b) described above is not particularly limited; and, filtration, centrifugation, an evaporation treatment by a rotary evaporator and the like can be included. After these, drying may be performed until the solvent portion is completely removed by further using a vacuum dryer or the like. A method of re-dispersing in a solvent used in the step (c) is not particularly limited, and, well-known, common methods such as a heat treatment, a stirring treatment, a dispersing and stirring treatment, a dispersing homogeneous treatment, an ultrasonic irradiation treatment, an ultrasonic stirring treatment, an ultrasonic homogeneous treatment or an ultrasonic dispersing treatment can be performed as one kind or as a combination of a plurality of kinds.

It is possible to obtain the phthalocyanine nano-sized one-dimensional structure in which the size-reduced complex obtained in the step (b) grows into the one-dimensional crystal by the method described above. On the other hand, by reducing the ratio of the major axis/the minor axis (the aspect ratio) of the nano-sized one-dimensional structure obtained in this manner, it is also possible to set the one-dimensional structure having proper aspect ratio. As a specific method, in an organic solvent, the nano-sized one-dimensional structure obtained by the method described above is subjected to the treatments in which the methods such as a stirring treatment, a dispersing and stirring treatment, a dispersion homogeneous treatment, an ultrasonic irradiation treatment, an ultrasonic stirring treatment, an ultrasonic homogeneous treatment, an ultrasonic dispersing treatment or a laser irradiation treatment are used as one kind or are used as a combination of a plurality of kinds. According to these treatments, it is possible to reduce the aspect ratio of the nano-sized one-dimensional structure to the proper size.

<Ink Composition>

An ink composition of the present invention contains the phthalocyanine nano-sized substance of the present invention and an organic solvent as an essential component. These ink compositions are suitable as a precursor material which forms an active part (a semiconductor layer) of the electronic element by the wet process (printing or coating).

The ink composition of the present invention is manufactured by dispersing the phthalocyanine nano-sized one-dimensional substance in an organic solvent. In addition, a dispersion liquid of the phthalocyanine nano-sized one-dimensional substance obtained in the step (c) described above can be also used as the ink composition of the present invention.

The type of the above organic solvent is not particularly limited as long as the phthalocyanine nano-sized one-dimensional substance can be stably dispersed, and the organic solvent alone or the organic solvent as a combination of two or more kinds thereof may be used, and, in terms of being able to be favorably and stably dispersed, for example, an amide-based organic solvent, an aromatic-based organic solvent, a halogen-based organic solvent, a glycol ester-based solvent, a glycol ether-based solvent, and the like having high affinity for phthalocyanines are preferable, and specifically, as an amide-based solvent, N,N-dimethylacetamide, N,N-dimethylformamide and N-methylpyrrolidone, as aromatic-based organic solvent, toluene, xylene and ethylbenzene, as a halogen-based organic solvent, chlorobenzene, dichlorobenzene, chloroform, methylene chloride and dichloroethane, as a glycol ester-based solvent, ethylene glycol monomethyl ether acetate, diethylene glycol monoethyl ether acetate, diethylene glycol monobutyl ether acetate and propylene glycol monomethyl ether acetate, and as a glycol ether-based solvent, ethylene glycol methyl ether, ethylene glycol ethyl ether, ethylene glycol butyl ether, diethylene glycol ethyl ether, diethylene glycol butyl ether, propylene glycol monomethyl ether, propylene glycol monoethyl ether, propylene glycol monopropyl ether, propylene glycol tertiary butyl ether, dipropylene glycol monomethyl ether can be included as the most suitable organic solvent for dispersion.

In the ink composition of the present invention, in order to impart the wet process aptitude (printability or coatability) and the film formability (the film quality performance after printing or coating), the content rate of the phthalocyanine nano-sized one-dimensional structure in the composition is preferably set to 0.05% by mass to 20% by mass, and is particularly preferably set to 0.1% by mass to 10% by mass.

The ink composition of the present invention may include other electron donating material or hole transport property material other than the phthalocyanine nano-sized one-dimensional structure. As such a material, for example, a π-conjugate-based polymer exhibiting the semiconducting property, a non-π-conjugate-based polymer exhibiting the semiconducting property, a low molecular based organic semiconductor compound, and the like are included. Here, polythiophene, poly(3-hexylthiophene-2,5-diyl) (P3HT), a P3HT Regio regular type, poly-p-phenylenevinylenes, poly-p-phenylenes, polyfluorenes, polypyrroles, polyanilines, polyacetylenes, polythienylenevinylenes, and the like as a n-conjugate-based polymer exhibiting the semiconducting property, polyvinyl carbazole as a non-π-conjugate-based polymer exhibiting the semiconducting property, and a soluble or a solvent dispersible phthalocyanine derivative, a soluble or a solvent dispersible porphyrin derivative, 6,13-bis(triisopropylsilylethynyl)pentacene (TIPS-pentacene), and the like as a low molecular based organic semiconductor compound can be included. Among those, a polymer-based material also has an effect which imparts the wet process aptitude (printability or coatability) and the film formability (the film quality performance after printing or coating) to the ink composition as described later.

The ink composition of the present invention may include an electron accepting material typified by fullerenes. Accordingly, when used in the photoelectric conversion element, it becomes possible to form an active part (a photoelectric conversion layer) by forming a film once. As an electron accepting material which can be used in the present invention, for example, a naphthalene derivative, a perylene derivative, an oxazole derivative, a triazole derivative, a phenanthroline derivative, a phosphine oxide derivative, fullerenes, a carbon nanotube (CNT), graphene, a derivative in which a cyano group is introduced into poly-p-phenylenevinylene (CN-PPV), Boramer (trade name, manufactured by TDA Research, Inc.), a well-known, common low molecular organic semiconductor material or high molecular organic semiconductor material in which $CF_3$ group or F group is introduced, and the like are included. Here, 1,4,5,8-naphthalene tetracarboxylic diimide (NTCDI), N,N'-dialkyl-1,4,5,8-naphthalene tetracarboxylic diimide (NTCDI-R) (an alkyl indicates an alkyl group having C1 to C18 carbon atoms), 1,4,5,8-naphthalene tetracarboxylic dianhydride (NTCDA), or the like as a naphthalene derivative, 3,4,9,10-perylene tetracarboxylic dianhydride (PTCDA), 3,4,9,10-perylene tetracarboxylic bisbenzimidazole (PTCBI), 3,4,9,10-perylene tetracarboxylic diimide (PTCDI), N,N'-dimethyl-3,4,9,10-perylene tetracarboxylic diimide (PTCDI-C1), N,N'-dipentyl-3,4,9,10-perylene tetracarboxylic diimide (PTCDI-C5), N,N'-dioctyl-3,4,9,10-perylene tetracarboxylic diimide (PTCDI-C8), N,N'-diphenyl-3,4,9,10-perylene tetracarboxylic diimide (PTCDI-Ph), or the like as a perylene derivative, 2-(4-biphenylyl)-5-(4-t-butylphenyl)-1,3,4-oxadiazole (PBD), 2,5-di(1-naphthyl)-1,3,4-oxadiazole (BND), or the like as an oxazole derivative, 3-(4-biphenylyl)-4-phenyl-5-(4-t-butylphenyl)-1,2,4-triazole (TAZ), or the like as a triazole derivative, bathocuproine (BCP), bathophenanthroline (Bphen), or the like as a phenanthroline derivative, and an unsubstituted fullerene such as C60, C70, C76, C78, C82, C84, C90, C94, and [6,6]-phenyl C61 butyric acid methyl ester (another name: PCBM or [60]PCBM), [6,6]-phenyl C61 butyric acid butyl ester (another name: PCBB), [6,6]-phenyl C61 butyric acid hexyl ester ([6,6]-PCBH), [6,6]-phenyl C61 butyric acid octyl ester (another name: PCB-C8), [6,6]-phenyl C61 butyric acid dodecyl ester ([6,6]-PCBD), [60]ThPCBM, (6,6)-phenyl C71 butyric acid methyl ester (another name: PC70BM or [70]PCBM), (6,6)-phenyl C85 butyric acid methyl ester (another name: PC84BM or [84]PCBM), or the like as fullerenes are included. Among those, fullerenes are preferably used since the charge separation rate and the electronic transfer rate are fast. Among fullerenes, PCBM and the C70 derivatives (PC70BM or the like described above) are more preferable since the charge separation rate and the electronic transfer rate are especially excellent and higher photoelectric conversion efficiency can be obtained.

In addition, among the electron accepting materials described above, a polymer-based material (an electron accepting polymer) such as a derivative in which a cyano group is introduced into poly-p-phenylenevinylene (CN-PPV), Boramer (trade name, manufactured by TDA Research, Inc.) is preferable since there is an effect of imparting the wet process aptitude (prinability or coatability) and the film formability (the film quality performance after printing or coating) to the above ink composition (or the material for photoelectric conversion element), in addition to the semiconducting properties such as the charge separation or the electronic transfer.

As to the mixture ratio of the phthalocyanine nano-sized one-dimensional structure of the ink composition of the present invention and the electron accepting material, it is possible to arbitrarily select the mixture ratio in a range in which the photoelectric conversion characteristics can be obtained in a photoelectric conversion element described later, and, a range of the phthalocyanine nano-sized one-dimensional structure/the electron accepting material=1/99 to 99/1 is preferable, a range of 1/9 to 9/1 is more preferable, and a range of 2/8 to 8/2 is further preferable.

In the ink composition of the present invention, in a case of adding the electron accepting material, the content ratio of the total amount of the above phthalocyanine nano-sized one-dimensional structure and the electron accepting material is preferably set to 0.05% by mass to 20% by mass, and particularly preferably set to 0.1% by mass to 10% by mass, with respect to the solvent.

In order to impart the wet process aptitude (printability or coatability) and the film formability (the film quality performance after printing or coating), a resin component as rheology adjustment or a binder component can be added to the ink composition of the present invention. As a resin, there is no particular limitation as long as it is a well-known, common resin, the resin may be used alone or as two or more kinds thereof may be used together, and, polymethylmethacrylate, polystyrene, polycarbonate, and the like are preferable.

When the content ratio of these resins is too high, the viscosity excessively increases, and thus the film formation property by printing and coating is affected, and since polymethylmethacrylate, polystyrene, polycarbonate, and the like are electrically inactive, when the content ratio thereof is too high, the concentration of the phthalocyanine nano-sized structure of the present invention relatively becomes diluted, and thus the semiconducting characteristics exhibited by the phthalocyanine nano-sized structure of the present invention are reduced. Therefore, the content ratio of the resin in the ink composition is preferably set to 20% by mass or less, and further preferably set to 10% by mass or less.

In the ink composition of the present invention, for a main purpose of improving the wet process aptitude (printability or catability) and the film formability (the film quality performance after printing or coating), the constitutional components, various kinds of surfactants, and the like can be added and used, as necessary.

As a constitutional component, a well-known, common particulate powder substance and a dispersion liquid in which these particulate powder substances are dispersed in a dispersant or an organic solvent in advance can be used as long as the semiconducting characteristics can be maintained, and the constitutional component may be used alone or as a combination of two or more kinds thereof. Specifically, AEROSIL series (trade name: manufactured by Evonik Industries), Silysia, Sylophobic, Sylopute, Sylopage, Sylopure, Sylosphere, Sylomask, Silwell, Fuji Balloon (all of which are trade names, manufactured by FUJI SILYSIA CHEMICAL LTD.), PMA-ST, IPA-ST (all of which are trade names, manufactured by NISSAN CHEMICAL INDUSTRIES, LTD.), NANOBIC 3600 series, NANOBIC 3800 series (all of which are trade names, manufactured by Byk-Chemie), and the like are included, and, there is no particular limitation. In addition, they may be used alone or as a combination of two or more kinds thereof. In addition, since the photoelectric conversion element transports a charge in the film thickness direction, the surface smoothness of the above film is required. Therefore, the average particle diameter of the constitutional component added to the ink is preferably from 1 nm to 150 nm and more preferably from 5 nm to 50 nm, and PMA-ST, IPA-ST (trade name, manufactured by NISSAN CHEMICAL INDUSTRIES, LTD.) and NANOBIC 3600 series (trade name, manufactured by Byk-Chemie) which are a fine particle silica and a alumina dispersion are preferred. The average particle diameter can be easily measured, for example, by a dynamic light scattering method. In addition, since these constitutional components are electrically inactive, when the content ratio thereof is too high, the concentration of the phthalocyanine nano-sized substance of the present invention relatively becomes diluted, and thus the semiconducting characteristics exhibited by the phthalocyanine nano-sized substance of the present invention are reduced. Therefore, the content ratio of the constitutional component in the ink composition is 90% by mass or less, and preferably 70% by mass or less, in the total solid content.

As a surfactant, a hydrocarbon-based one, a silicon-based one and a fluorine-based one are included and they can be used alone or as a combination of two or more kinds thereof. Among those, a preferred fluorine-based surfactant is a nonionic-based fluorine-based surfactant having a linear perfluoroalkyl group in which the chain length is C6 or more and further preferably C8 or more. As a specific one, for example, MEGAFAC F-482, MEGAFAC F-470 (R-08), MEGAFACF-472SF, MEGAFAC R-30, MEGAFAC F-484, MEGAFAC F-486, MEGAFAC F-172D, MEGAFAC F178RM (all of which are trade names, manufactured by DIC Corporation), and the like are included, and, there is no particular limitation. They may be used alone or as a combination of two or more kinds thereof. 5.0% by mass or less of the surfactant as an active ingredient, and preferably 1.0% by mass or less as an active ingredient are contained in the ink composition.

In the ink composition of the present invention, the materials described above are mixed and used. A mixing method is not particularly limited, and, a method in which the materials described above are added to a solvent in the desired ratio and then the materials are dispersed and mixed in a solvent by using one kind or combining a plurality of kinds of methods such as well-known, common methods, in other words, a heat treatment, a stirring treatment, a dispersing and stirring treatment, a dispersing homogeneous treatment, an ultrasonic irradiation treatment, an ultrasonic stirring treatment, an ultrasonic homogeneous treatment, an ultrasonic dispersing treatment and a laser irradiation treatment is included.

<Electronic Element>

Next, description will be given of an electronic element of the present invention. The electronic element of the present invention is an electronic element which contains the phthalocyanine nano-sized one-dimensional structure of the present invention in an active layer unit (a semiconductor layer). As a specific example of the electronic element, a photoelectric conversion element such as a solar cell or a light-receiving element, a transistor such as a field effect transistor, a static induction transistor or a bipolar transistor, an electroluminescence element, a temperature sensor, a gas sensor, a humidity sensor, a radiation sensor, and the like are included, and, the electronic element is not limited thereto.

<Photoelectric Conversion Element>

Next, description will be given of a photoelectric conversion element of the present invention. The photoelectric conversion element of the present invention has at least a pair of electrodes, that is, a positive electrode and a negative electrode, and the phthalocyanine nano-sized substance of the present invention is included between these electrodes. FIG. 1 is a schematic diagram illustrating an example of a photoelectric conversion element of the present invention. In FIG. 1, the reference sign 1 is a substrate, the reference sign 2 is an electrode a, the reference sign 3 is a photoelectric conversion layer (an organic semiconductor layer) including the phthalocyanine nano-sized substance of the present invention, and the reference sign 4 is an electrode b.

The organic semiconductor layer 3 is a film including the phthalocyanine nano-sized one-dimensional structure of the present invention. In addition, the organic semiconductor layer 3 is a film formed by the ink composition of the present invention.

Figure 2:
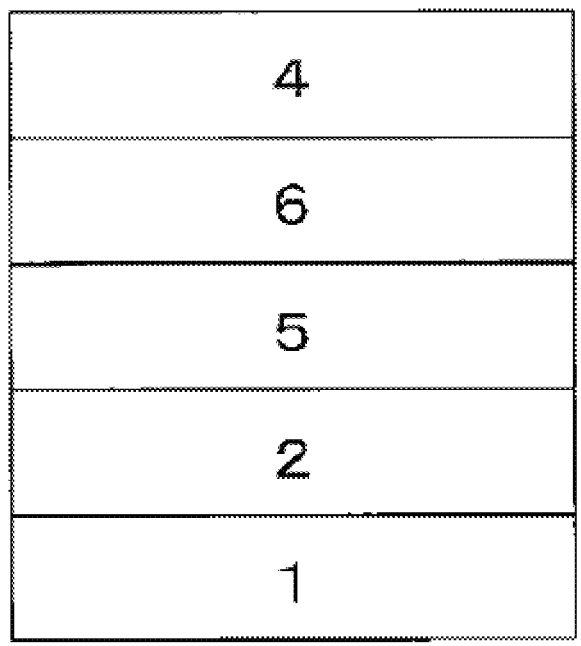
FIG. 2 is a schematic cross-section of a photoelectric conversion element according to the present invention.

In a case where the organic semiconductor layer 3 include the electron accepting material, the phthalocyanine nano-sized substance of the present invention and the electron accepting material may be mixed or layer-by-layer laminated. An example of a case of being layer-by-layer laminated is shown in FIG. 2. It is preferred that a layer having the phthalocyanine nano-sized substance of the present invention which is the electron donating material be the positive electrode side and a layer having the electron accepting material be the negative electrode side. Therefore, in a case where the reference sign 5 is a layer having the phthalocyanine nano-sized one-dimensional structure of the present invention and the reference sign 6 is a layer having the electron accepting material in FIG. 2, the electrode a of the reference sign 2 is a positive electrode and the electrode b of the reference sign 4 is a negative electrode. Moreover, in a case of a laminated structure, "other electron donating materials other than the phthalocyanine nano-sized one-dimensional structure described above" may be contained in the layer including the phthalocyanine nano-sized substance of the present invention (the reference sign 5) or may be contained in the layer including the electron accepting material (the reference sign 6).

The thickness of the organic semiconductor layer (the reference sign 3 in FIG. 1 and the reference signs 5 and 6 in FIG. 2) is not particularly limited as long as the thickness is a thickness in which a light can be sufficiently absorbed and the deactivation of a charge does not occur, and, the thickness is preferably in a range from 5 nm to 1,000 nm, more preferably from 10 nm to 500 nm, and further preferably from 20 nm to 300 nm. In a case of being layer-by-layer laminated, the layer having the phthalocyanine nano-sized substance of the present invention has preferably the thickness of 1 nm to 500 nm and more preferably the thickness of 5 nm to 300 nm, of the thickness described above.

The organic semiconductor layer can be obtained by forming a film using the ink composition of the present invention by the wet process (printing or coating) and drying the film. As a film formation method of the ink composition of the present invention, there is no particular limitation and well-known, common methods can be employed, and specifically, an ink jet method, a gravure printing method, a gravure offset printing method, an offset printing method, a letterpress printing method, a letterpress reversed printing method, a screen printing method, a microcontact printing method, a reverse coater method, an air doctor coater method, a blade coater method, an air knife coater method, a roll coater method, a squeeze coater method, an immersion coater method, a transfer roll coater method, a kiss coater method, a cast coater method, a spray coater method, an electrostatic coater method, an ultrasonic spray coater method, a die coater method, a spin coater method, a bar coater method, a slit coater method, a drop cast method, and the like are included.

In a case where the organic semiconductor layer is layer-by-layer laminated in the way as shown in FIG. 2, after the film is formed using the ink composition of the present invention including the phthalocyanine nano-sized one-dimensional structure by the method described above, the electron accepting material has to be laminated by the same well-known, common method as those for a film formation of a buffer layer described later. Moreover, it is important to mention that it is possible to laminate the electron accepting material by the wet process since the solvent resistance of the phthalocyanine nano-sized substance of the present invention increases after the film formation.

Silicon, glass, various kinds of resin materials and the like can be used for the substrate 1. As various kinds of resin materials, for example, polyethylene terephthalate (PET), polyethylene naphthalate (PEN), polyether sulfone (PES), polyetherimide, polyetheretherketone, polyphenylene sulfide, polyarylate, polyimide, polycarbonate (PC), cellulose triacetate (TAC), cellulose acetate propionate (CAP), an acrylic resin, and the like can be included. By using such resin materials, it is possible to achieve the weight reduction and enhance the portability as well as to improve the resistance to impact, compared with a case of using glass.

On the other hand, in a case of entering light from the substrate side, a material having excellent optical transparency is preferable, and as such the material, glass, PET, PC, polyimide, PES, an acrylic resin, and the like can be included.

As a material for the electrode a and b, it is preferred that a conductive material having a large work function be used for one electrode and a conductive material having a small work function be used for the other electrode. The electrode using the conductive material having a large work function becomes a positive electrode. As the conductive material having a large work function, indium having the transparency, a metal oxide such as tin, a combined metal oxide (an indium tin oxide (ITO), an indium zinc oxide (IZO), a fluorine-doped tin oxide (FTC)), (a few layer) graphene, (a few layer) modified graphene, and a general well-known conductive polymer in which the conductivity is improved by doping (a conductive polyaniline, a conductive polypyrrole, a conductive polythiophene, polyethylenedioxythiophene (PEDOT)), are preferably used, in addition to a metal such as gold, platinum, chromium or nickel. Here, the conductive material which is used for the positive electrode is preferably one which is ohmic contact to the organic semiconductor layer 3. Furthermore, in a case where a buffer layer 1 described later is used, the conductive material which is used for the positive electrode is preferably one which is ohmic contact to the buffer layer 1.

The electrode using the conductive material having a small work function becomes a negative electrode, and as the conductive material having a small work function, an alkali metal and an alkali earth metal, specifically, lithium, magnesium, calcium, and the like are used. In addition, tin, silver, aluminum, and the like are preferably used. Furthermore, an electrode composed of a laminated body, composed of both an alloy composed of the metal described above and the metal described above, are also preferably used. Here, the conductive material which is used for the negative electrode is preferably one which is ohmic contact to the organic semiconductor layer 3. Furthermore, in a case where a buffer layer 2 described later is used, the conductive material which is used for the negative electrode is preferably one which is ohmic contact to the buffer layer 2.

In the photoelectric conversion element of the present invention, either the electrode a or the electrode b has preferably the optical transparency. The optical transparency of the electrode is not particularly limited as long as the optical transparency is an optical transparency of the degree that incident light reaches the organic semiconductor layer 3 to generate an electromotive force. As such the conductive material, for example, among the conductive materials described above, ITO (an indium oxide-tin oxide complex), FTO (a fluorine-doped tin oxide), (a few layer) graphene, (a few layer) modified graphene, and a general well-known conductive polymer in which the conductivity is improved by doping (a conductive polyaniline, a conductive polypyrrole, a conductive polythiophene, polyethylenedioxythiophen (PEDOT), and the like) are preferably used. In addition, these materials can be used in combination with a mesh-like metal material having high conductivity.

The thickness of the electrode has to be in a range having the optical transparency and the conductivity and the thicknesses are different depending on the electrode materials, and, the thickness is from 5 nm to 10,000 nm, preferably from 10 nm to 5,000 nm, and further preferably from 20 nm to 300 nm. Moreover, as long as the other electrode has the conductivity, it is not necessary for the other electrode to have the optical transparency and the thickness thereof is not particularly limited.

As a method of forming an electrode, by using the materials described above as a raw material, a dry process such as a vacuum evaporation method, a molecular beam epitaxial growth method, an ion cluster beam method, a low energy ion beam method, an ion plating method, a CVD method, a sputtering method, an atmospheric pressure plasma method and a wet process such as an ink jet method, a gravure printing method, a gravure offset printing method, an offset printing method, a letterpress printing method, a letterpress reversed printing method, a screen printing method, a microcontact printing method, a reverse coater method, an air doctor coater method, a blade coater method, an air knife coater method, a roll coater method, a squeeze coater method, an immersion coater method, a transfer roll coater method, a kiss coater method, a cast coater method, a spray coater method, an electrostatic coater method, an ultrasonic spray coater method, a die coater method, a spin coater method, a bar coater method, a slit coater method or a drop cast method are included, and they can be appropriately used according to the materials. In more detail, a method of forming an electrode through a pattern mask or the like using a dry process such as evaporation or sputtering, a method of forming an electrode by a well-known, common photolithography method-etching method using a conductive solid film formed by a dry process such as evaporation or sputtering, a method of forming an electrode by combining a dry process such as evaporation or sputtering and a photolithography method-a lift-off method, and a method of etching, by using a resist by an ink jet or the like, a conductive solid film formed by using a dry process such as evaporation or sputtering, are included. In addition, it may be directly performed to pattern by a wet process using a conductive fine particle dispersion liquid, or a conductive polymer solution or dispersion liquid, a wet process such as an ink jet method, a screen printing method, a gravure offset printing method, a letterpress reversed printing method or a microcontact printing method. Also, patterning may be performed by a well-known, common photolithography method-etching method, a laser ablation method, or the like after a solid film is formed by coating to form a film, or patterning may be performed by combining a wet process and a photolithography method-a lift-off method.

In the photoelectric conversion element of the present invention, the buffer layer 1 may exist between the positive electrode and the organic semiconductor layer. The buffer layer 1 is used as necessary, in order to be able to effectively collect a charge. As a material which forms the buffer layer 1, a graphene oxide, a modified graphene, polythiophenes, polyanilines, poly-p-phenylenevinylenes, polyfluorenes, polyvinyl carbazoles, a phthalocyanine derivative (H2Pc, CuPc, ZnPc, or the like), a porphyrin derivative, and the like are preferably used. These materials may be one in which the conductivity (the hole transport properties) is enhanced by doping. In particular, polyethylene dioxythiophene (PEDOT) which are polythiophenes and PEDOT: PSS in which PEDOT is doped with polystyrene sulfonate (PSS) are preferably used. The thickness of the buffer layer 1 is preferably the thickness from 5 nm to 600 nm and more preferably from 10 nm to 200 nm.

In addition, in the photoelectric conversion element of the present invention, the buffer layer 2 may exist between the organic semiconductor layer and the negative electrode. The buffer layer 2 is used as necessary, in order to be able to effectively collect a charge. As a material which forms the buffer layer 2, octa azaporphyrin, a perfluoro compound such as perfluoropentacene or perfluorophthalocyanine, a charge transfer complex composed of an electron donating compound such as tetrathiofulvalene or tetramethyl phenylenediamine and an electron accepting compound such as tetracyanoquinodimethane or tetracyanoethylene, n type inorganic oxide semiconductor such as titanium oxide, zinc oxide or gallium oxide, an alkali metal compound such as lithium fluoride, sodium fluoride, or cesium fluoride, and the like can be used, in addition to the electron accepting material described above (a naphthalene derivative, a perylene derivative, an oxazole derivative, a triazole derivative, a phenanthroline derivative, a phosphine oxide derivative, fullerenes, carbon nanotubes (CNT), modified graphenes, a derivative in which a cyano group is introduced into poly-p-phenylenevinylene (CN-PPV), Boramer (trade name, manufactured by TDA Research, Inc.), a well-known, common low molecular organic semiconductor material or high molecular organic semiconductor material in which $CF_3$ group or F group is introduced, or the like). The thickness of the buffer layer 2 is preferably the thickness from 0.5 nm to 600 nm and more preferably from 1 nm to 200 nm.

As a method of forming a buffer layer, a dry process such as a vacuum evaporation method, a molecular beam epitaxial growth method, an ion cluster beam method, a low energy ion beam method, an ion plating method, a CVD method, a sputtering method or an atmospheric pressure plasma method and a wet process such as an inkjet method, a gravure printing method, a gravure offset printing method, an offset printing method, a letterpress printing method, a letterpress reversed printing method, a screen printing method, a microcontact printing method, a reverse coater method, an air doctor coater method, a blade coater method, an air knife coater method, a roll coater method, a squeeze coater method, an immersion coater method, a transfer roll coater method, a kiss coater method, a cast coater method, a spray coater method, an electrostatic coater method, an ultrasonic spray coater method, a die coater method, a spin coater method, a bar coater method, a slit coater method or a drop cast method are included, and they can be appropriately used according to the materials.

In addition, in a case where an inorganic oxide is used for the buffer layer, as a wet process, a method of drying after applying a liquid in which fine particles of the inorganic oxide are dispersed in an arbitrary organic solvent or water, using a dispersing adjuvant such as a surfactant or the like as necessary, or the so-called sol-gel method of drying after applying a solution of an oxide precursor, such as an alkoxide, can be used.

These buffer layers may be a single layer or may be formed by layer-by-layer laminating different materials.

The photoelectric conversion element according to the present invention can configure a solar cell module by integration. At that time, the photoelectric conversion element of the present invention can be also set to a structure in which the photoelectric conversion element described above is insulated from the outside air containing water by a protective sheet or an adhesive sealing agent. As a solar cell module, a solar cell module which is characterized by integration the photoelectric conversion element according to the present invention by connecting in series, by the electrode a of the photoelectric conversion element according to the present invention coming into contact with the electrode b of other photoelectric conversion element adjacent thereto according to the present invention can be included.

In addition, the solar cell module may be a solar cell module which is characterized by integration the photoelectric conversion element according to the present invention by connecting in parallel, by coming into contact with each electrode a of the adjacent photoelectric conversion element according to the present invention and coming into contact with each electrode b of the adjacent photoelectric conversion element according to the present invention.

(Transistor)

Next, description will be given of a transistor of the present invention. The transistor of the present invention is a transistor containing the phthalocyanine nano-sized substance of the present invention in an active part (which is called a channel (a semiconductor layer) in a transistor).

As such a transistor, a top gate type in which a film containing the phthalocyanine nano-sized substance according to the present invention, and a source electrode and a drain electrode which are linked thereto are formed on the substrate, and a gate electrode is formed thereon through a gate insulator film can be included.

In addition, a bottom gate type in which a gate electrode is firstly formed on the substrate, and a film containing the phthalocyanine nano-sized substance according to the present invention, and a source electrode and a drain electrode which are linked thereto are formed through a gate insulator film can be also set.

Figure 3:
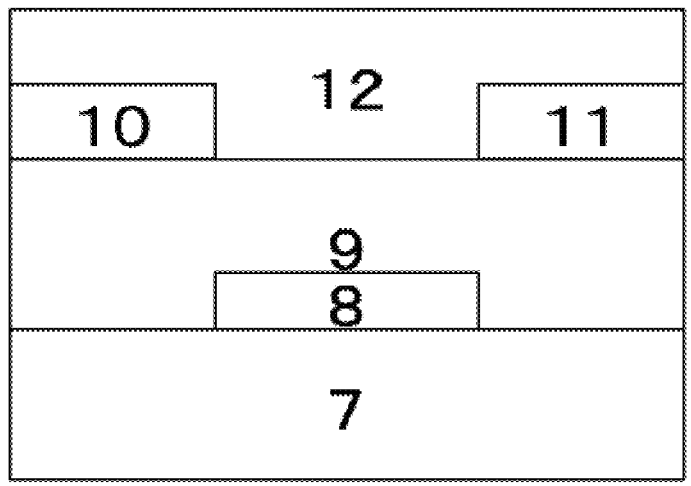
FIG. 3 is a schematic cross-section of a transistor according to the present invention.

In FIG. 3, as a transistor having a film containing the phthalocyanine nano-sized substance according to the present invention (12), a schematic diagram of a transistor which is configured with a bottom gate bottom contact type is shown. Here, the thickness of the film containing the phthalocyanine nano-sized substance of the present invention (12) can be appropriately set, and for example, the thickness can be set to 50 nm to 10,000 nm.

As a substrate 7, silicon, glass, a flexible resin-made sheet (a plastic film), and the like can be used. As the plastic film described above, for example, a film and the like composed of polyethylene terephthalate (PFT), polyethylene naphthalate (PEN), polyether sulfone (PES), polyetherimide, polyetheretherketone, polyphenylene sulfide, polyarylate, polyimide, polycarbonate (PC), cellulose triacetate (TAC), cellulose acetate propionate (CAP), or the like are included. In this manner, by using the plastic film, it is possible to achieve the weight reduction and to enhance the portability, as well as to improve the resistance to impact, compared with a case of using glass substrate.

A material which forms a source electrode 10, a drain electrode 11 and a gate electrode 8 is not particularly limited as long as the material is a conductive material, and platinum, gold, silver, nickel, chromium, copper, iron, tin, lead antimony, tantalum, indium, palladium, tellurium, rhenium, iridium, aluminum, ruthenium, germanium, molybdenum, tungsten, antimony tin oxide, indium•tin oxide (ITO), fluorine-doped zinc oxide, zinc, carbon, graphite, glassy carbon, a silver paste and a carbon paste, lithium, beryllium, sodium, magnesium, potassium, calcium, scandium, titanium, manganese, zirconium, gallium, niobium, a sodium-potassium alloy, a magnesium/copper mixture, a magnesium/silver mixture, a magnesium/aluminum mixture, a magnesium/indium mixture, an aluminum/aluminum oxide mixture, a lithium/aluminum mixture, and the like can be used, and, in particular, platinum, gold, silver, copper, aluminum, indium, ITO and carbon are preferable. In addition, a general well-known conductive polymer in which the conductivity is improved by doping or the like, for example, a conductive polyaniline, a conductive polypyrrole, a conductive polythiophene, a complex of polyethylenedioxythiophene and polystyrene sulfonic acid, and the like are favorably used. Among those, gold, silver, platinum, copper, a conductive polymer and ITO in which the electric resistance is low on the contact surface with the semiconductor layer are preferable.

As a method of forming an electrode, the same method as those for the electrode of the photoelectric conversion element described above can be used.

As a gate insulator film 9, various kinds of insulator films can be used. In consideration with cost benefit, a polymer-based organic material is preferably used, and in order to obtain high performance, the use of an inorganic oxide having high relative permittivity is preferable. As a polymer-based organic material, a well-known, common polymer such as polyimide, polyamide, polyester, polyacrylate, a photo-radical polymerization-based or a photo-cation polymerization-based photo-curing resin or copolymer containing an acrylonitrile component, polyvinyl phenol, polyvinyl alcohol, a novolac resin, an epoxy resin or cyanoethylpullulan can be used. As an inorganic oxide, silicon oxide, aluminum oxide, tantalum oxide, titanium oxide, tin oxide, vanadium oxide, barium strontium titanate, barium zirconate titanate, lead zirconate titanate, lead lanthanum titanate, strontium titanate, barium titanate, barium magnesium fluoride, bismuth titanate, strontium bismuth titanate, strontium bismuth tantalate, bismuth tantalate niobate, yttrium trioxide, and the like are included. Among those, silicon oxide, aluminum oxide, tantalum oxide, titanium oxide are preferable. An inorganic nitride such as silicon nitride or aluminum nitride can be favorably also used.

As a method of forming the insulator film described above, a dry process such as a vacuum evaporation method, a molecular beam epitaxial growth method, an ion cluster beam method, a low energy ion beam method, an ion plating method, a CVD method, a sputtering method or an atmospheric pressure plasma method and a wet process such as an ink jet method, a gravure printing method, a gravure offset printing method, an offset printing method, a letterpress printing method, a letterpress reversed printing method, a screen printing method, a microcontact printing method, a reverse coater method, an air doctor coater method, a blade coater method, an air knife coater method, a roll coater method, a squeeze coater method, an immersion coater method, a transfer roll coater method, a kiss coater method, a cast coater method, a spray coater method, an electrostatic coater method, an ultrasonic spray coater method, a die coater method, a spin coater method, a bar coater method, a slit coater method or a drop cast method are included, and, when a precise patterning is required, the wet process such as an ink jet method, a letterpress reversed printing method or a microcontact printing method are favorably used and they can be appropriately used according to the materials.

In addition to this, as a wet process of an inorganic oxide, a method of drying after applying a liquid in which fine particles of the inorganic oxide are dispersed in an arbitrary organic solvent or water, using a dispersing adjuvant such as a surfactant or the like as necessary, or the so-called sol-gel method of drying after applying a solution of an oxide precursor, such as an alkoxide, can be used.

The dried film thickness of these insulator films is from 0.1 μm to 2 μm and preferably 0.3 μm to 1 μm.

Figure 4:
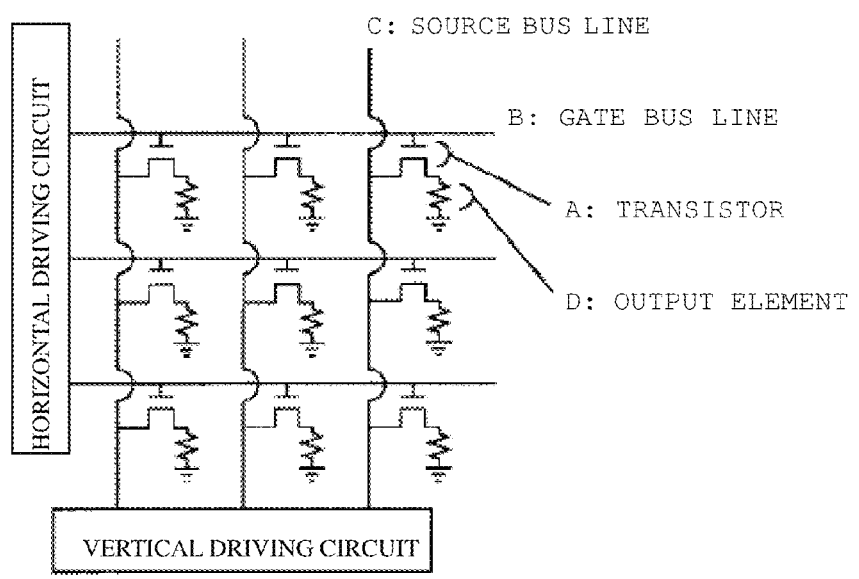
FIG. 4 is a schematic plan equivalent circuit diagram of a transistor array including a transistor according to the present invention.

The transistor which is the photoelectric element according to the present invention can configure an electronic part module by integration. As a electronic part module, a transistor array which is a back substrate of a display or the like (refer to FIG. 4), an inverter or a ring oscillator which is a logic circuit of RFID, and the like are included.

EXAMPLE

Hereinafter, more specifically, description will be given based on Examples of the present invention. And, the present invention is not limited to Examples described below.

Synthesis Example 1

After a mixture solution of 50 parts by mass of copper phthalocyanine-sulfonic acid (EXT-795 manufactured by DIC Corporation, the average degree of the sulfonation=0.95) and 1,000 parts by mass of DMF was cooled down to 5° C., 50 parts by mass of thionyl chloride was added dropwise and the reaction was performed at room temperature for 1 hour and then at 70° C. for 5 hours. After the reaction liquid was poured into 5,000 parts by mass of iced water, the obtained precipitate was collected and dried, a mixture of copper phthalocyanine-sulfonic acid and copper phthalocyanine sulphonyl chloride was obtained.

Next, 20 parts by mass of the mixture obtained as above was slowly put into a mixture of 23 parts by mass of 40% methyl monoamine aqueous solution (manufactured by TOKYO CHEMICAL INDUSTRY CO., LTD.), 20 parts by mass of sodium carbonate and 800 parts by mass of water and the reaction was performed at room temperature for 6 hours. 2,000 parts by mass of THF was added to the reaction liquid, the filtration was performed through a silica gel column of 5 cm and the filtrate was concentrated. The residue was added to a silica gel column, a fraction which was eluted by chloroform was collected and concentrated, and the compound represented by [Chem. 11] described below was obtained.

[Chem. 11]

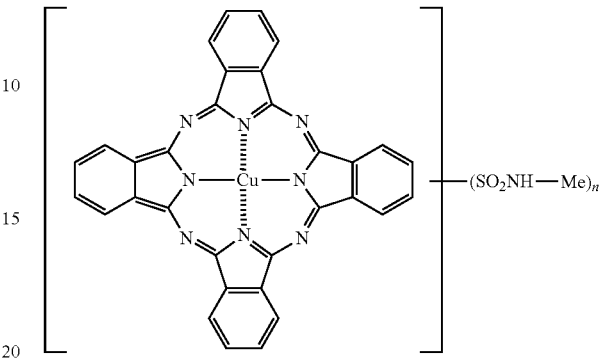

(Average number of introduced substituents n=1.1)

Synthesis Example 2

By performing the same operation as the synthesis example 1 except for using 17.5 parts by mass of n-propyl monoamine (manufactured by TOKYO CHEMICAL INDUSTRY CO., LTD.) instead of 23 parts by mass of 40% methyl monoamine aqueous solution used in the synthesis example 1, the compound represented by [Chem. 12] described below was obtained.

[Chem. 12]

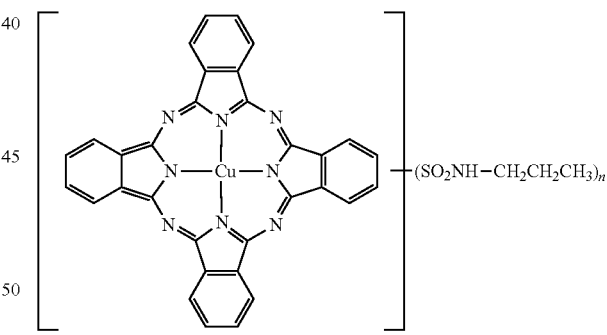

(Average number of introduced substituents n=1.1)

Synthesis Example 3

By performing the same operation as the synthesis example 1 except for using 30 parts by mass of hexyl monoamine (manufactured by TOKYO CHEMICAL INDUSTRY CO., LTD.) instead of 23 parts by mass of 40% methyl monoamine aqueous solution used in the synthesis example 1, the compound represented by [Chem. 13] described below was obtained.

[Chem. 13]

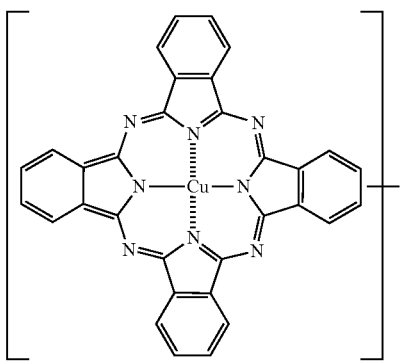

(Average number of introduced substituents n=1.1)

Synthesis Example 4

By performing the same operation as the synthesis example 1 except for using 55 parts by mass of dodecyl monoamine (manufactured by TOKYO CHEMICAL INDUSTRY CO., LTD.) instead of 23 parts by mass of 40% methyl monoamine aqueous solution used in the synthesis example 1, the compound represented by [Chem. 14] described below was obtained.

[Chem. 14]

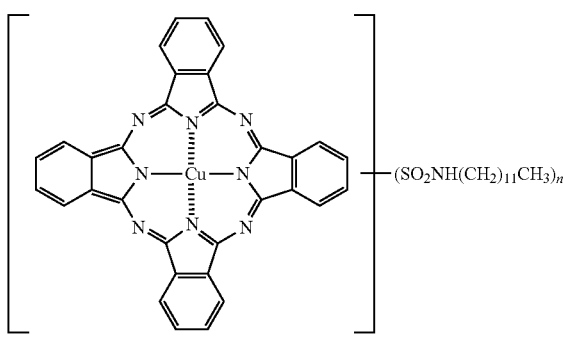

(Average number of introduced substituents n=1.1)

Synthesis Example 5

By performing the same operation as the synthesis example 1 except for using 80 parts by mass of stearyl monoamine (manufactured by TOKYO CHEMICAL INDUSTRY CO., LTD.) instead of 23 parts by mass of 40% methyl monoamine aqueous solution used in the synthesis example 1, the compound represented by [Chem. 15] described below was obtained.

[Chem. 15]

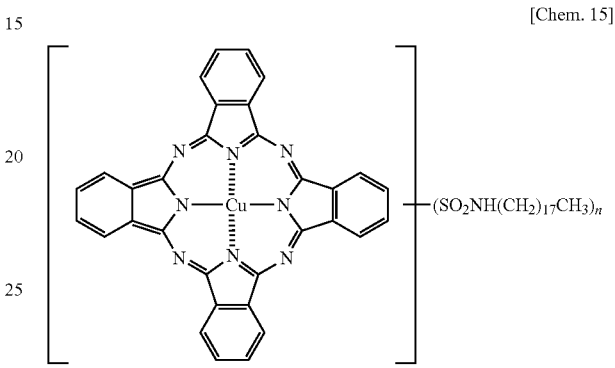

(Average number of introduced substituents n=1.1)

Synthesis Example 6

By performing the same operation as the synthesis example 1 except for using 29.4 parts by mass of cyclohexyl monoamine (manufactured by TOKYO CHEMICAL INDUSTRY CO., LTD.) instead of 23 parts by mass of 40% methyl monoamine aqueous solution used in the synthesis example 1, the compound represented by [Chem. 16] described below was obtained.

[Chem. 16]

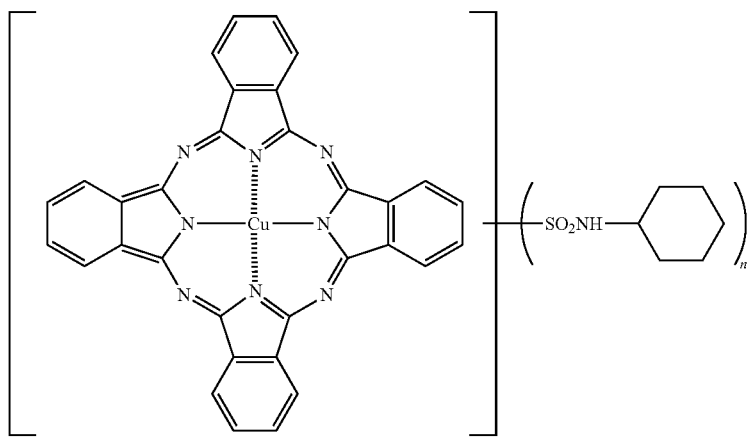

(Average number of introduced substituents n=1.1)

Synthesis Example 7

By performing the same operation as the synthesis example 1 except for using 27.6 parts by mass of phenyl monoamine (manufactured by TOKYO CHEMICAL INDUSTRY CO., LTD.) instead of 23 parts by mass of 40% methyl monoamine aqueous solution used in the synthesis example 1, the compound represented by [Chem. 17] described below was obtained.

[Chem. 17]

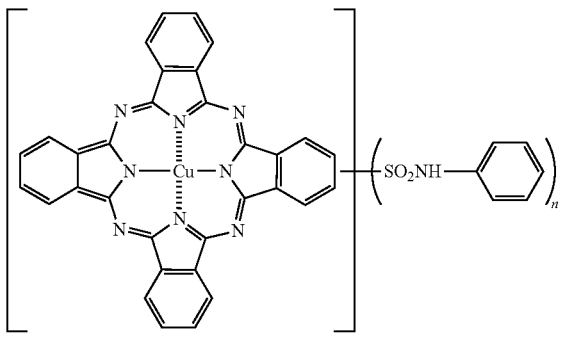

(Average number of introduced substituents n=1.1)

Synthesis Example 8

By performing the same operation as the synthesis example 1 except for using 29.4 parts by mass of 3-thienyl monoamine instead of 23 parts by mass of 40% methyl monoamine aqueous solution used in the synthesis example 1, the compound represented by [Chem. 18] described below was obtained.

[Chem. 18]

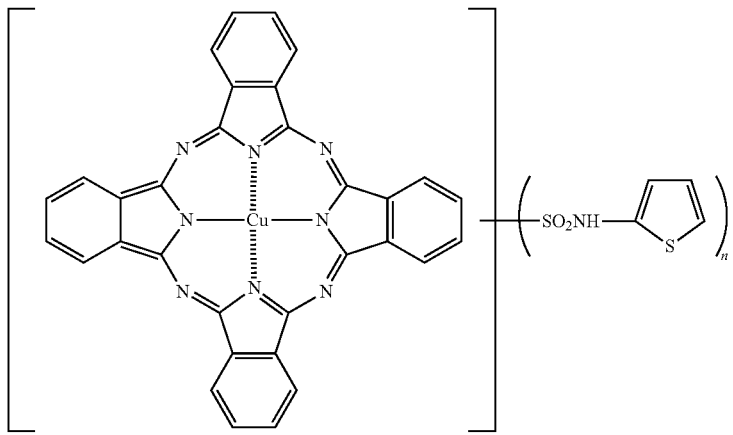

(Average number of introduced substituents n=1.1)

Example 1

<Manufacturing of Phthalocyanine Nano-sized Substance and Phthalocyanine Nano-sized Substance Dispersion Liquid>

1.6 g of copper phthalocyanine (Fastogen Blue 5380E (trade name, manufactured by DIC Corporation)) as unsubstituted phthalocyanine and 1.2 g of the phthalocyanine derivative which was obtained in the synthesis example 1 and was represented by [Chem. 11] as phthalocyanine having a substituent were put into 81 g of concentrated sulfuric acid (manufactured by KANTO CHEMICAL CO., INC.) and were completely dissolved, and the concentrated sulfuric acid solution was prepared. Subsequently, after 730 g of distilled water was put into a 1,000-mL beaker and was sufficiently cooled using iced water, the concentrated sulfuric acid solution which was prepared in advance was added while the above distilled water was stirred and a complex composed of unsubstituted copper phthalocyanine and a copper phthalocyanine derivative represented by [Chem. 11] was precipitated.

Subsequently, the above obtained complex was filtrated by using filter paper and was sufficiently washed by using distilled water, and afterward, the dehydration treatment was conducted by a vacuum dryer.

12 g of the complex described above composed of unsubstituted copper phthalocyanine and the copper phthalocyanine derivative represented by [Chem. 11] was put into a 50-ml, polypropylene-made container, dichlorobenzene was further added, the weight ratio of the above complex (the solid content) to dichlorobenzene was set to 10% (the solid content concentration 10%), next 60 g of zirconia beads having $\phi$ 0.5 mm were added and the dispersion treatment was conducted by using a paint shaker for 2 hours (the size-reduction of the complex). Subsequently, the dispersion liquid of the seze-reduced complex was separated and collected from zirconia beads, dichlorobenzene was further added, and the solid content concentration was diluted to 2% (preparation of 2% dichlorobenzene dispersion liquid of the size-reduced complex).

Next, 10 g of 2% dichlorobenzene dispersion liquid of the size-reduced complex described above was fractionated into a pressure resistant vessel and was heated up to 200° C. over 90 minutes. After reaching 200° C., 2% dichlorobenzene dispersion liquid of the size-reduced complex was continuously heated for another 30 minutes at the same temperature and afterward, was cooled. In this manner, the phthalocyanine nano-sized substance which is phthalocyanine exhibiting one-dimensional crystal growth on a nano-size was obtained in a state in which it was dispersed in dichlorobenzene with 2% solid content concentration (phthalocyanine nano-sized substance dispersion liquid (1)).

Figure 5:
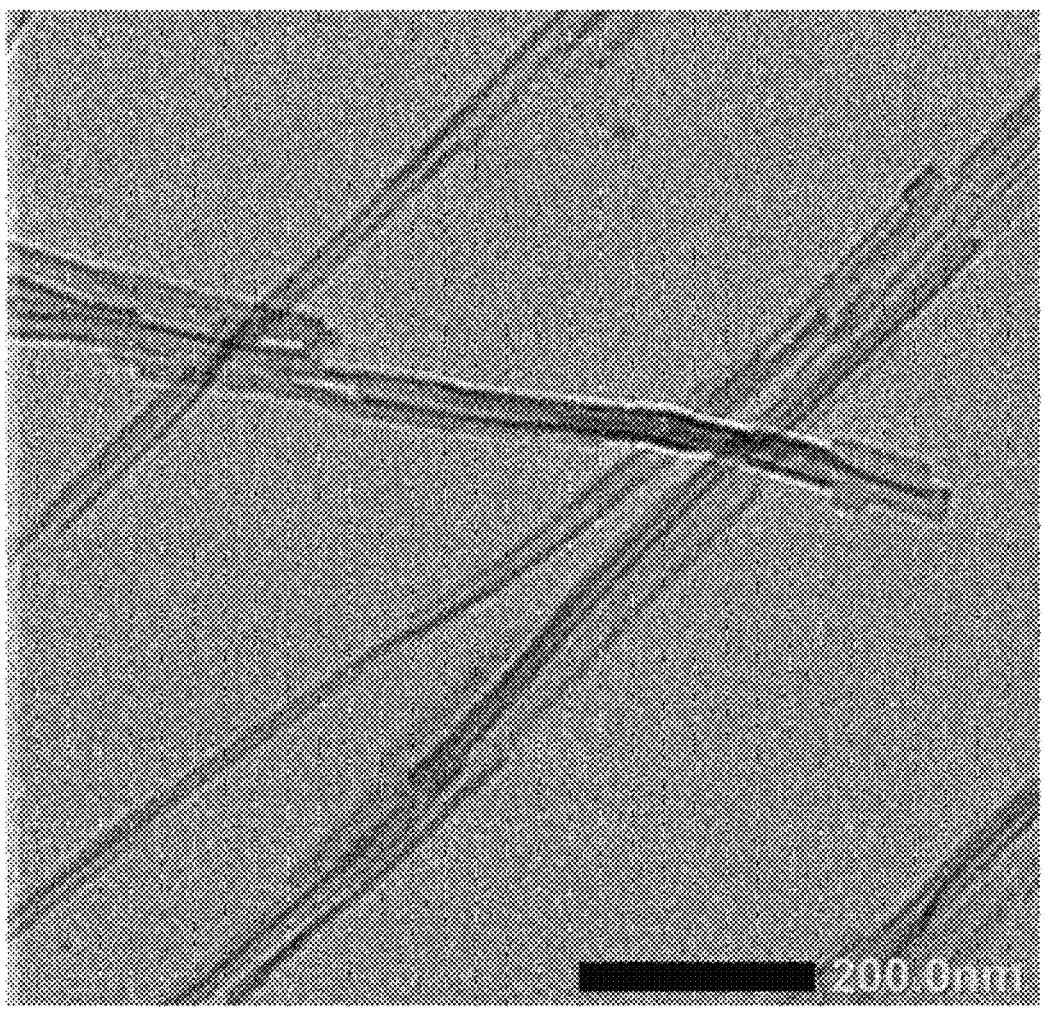
FIG. 5 is a transmission electron microscopic image of a solid content in a phthalocyanine nano-sized substance dispersion liquid (1).
Figure 6:
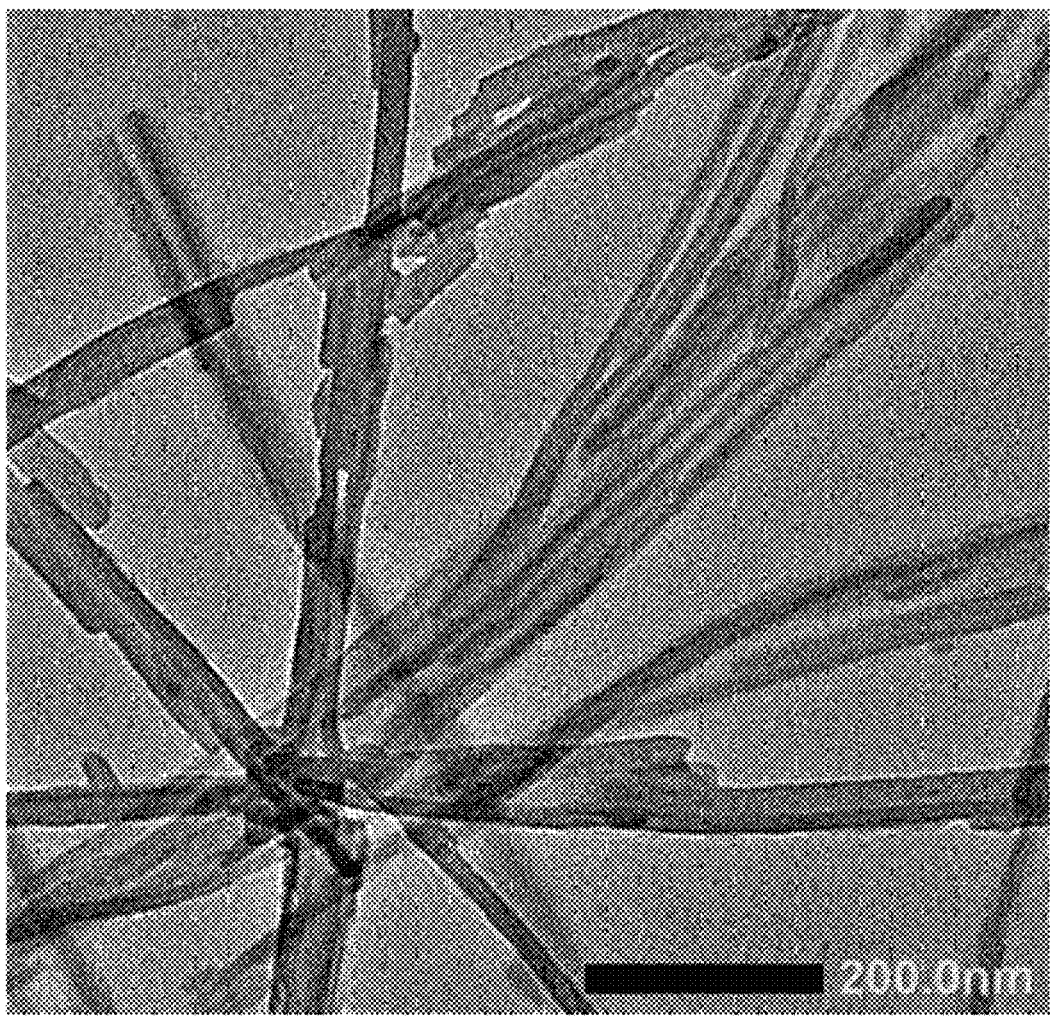
FIG. 6 is a transmission electron microscopic image of a solid content in a phthalocyanine nano-sized substance dispersion liquid (2).
Figure 7:
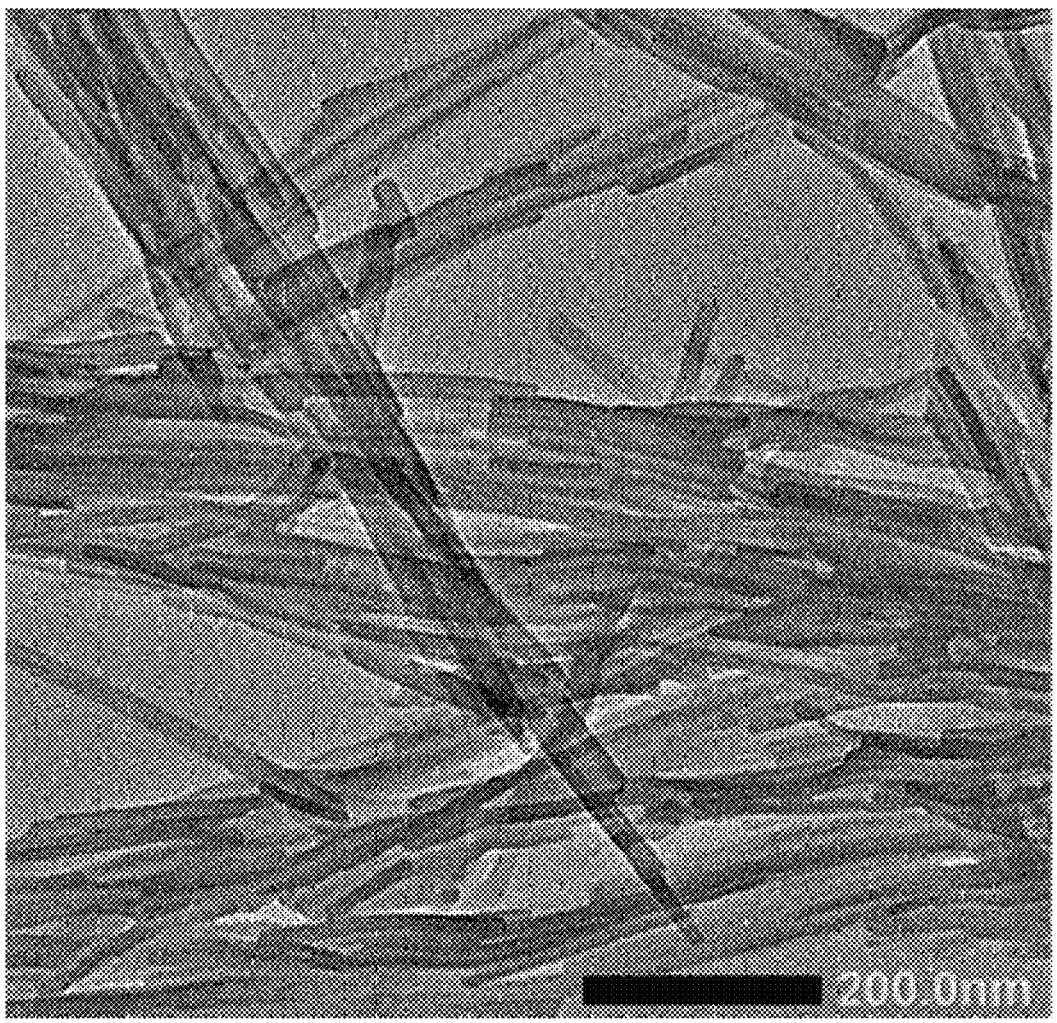
FIG. 7 is a transmission electron microscopic image of a solid content in a phthalocyanine nano-sized substance dispersion liquid (3).
Figure 8:
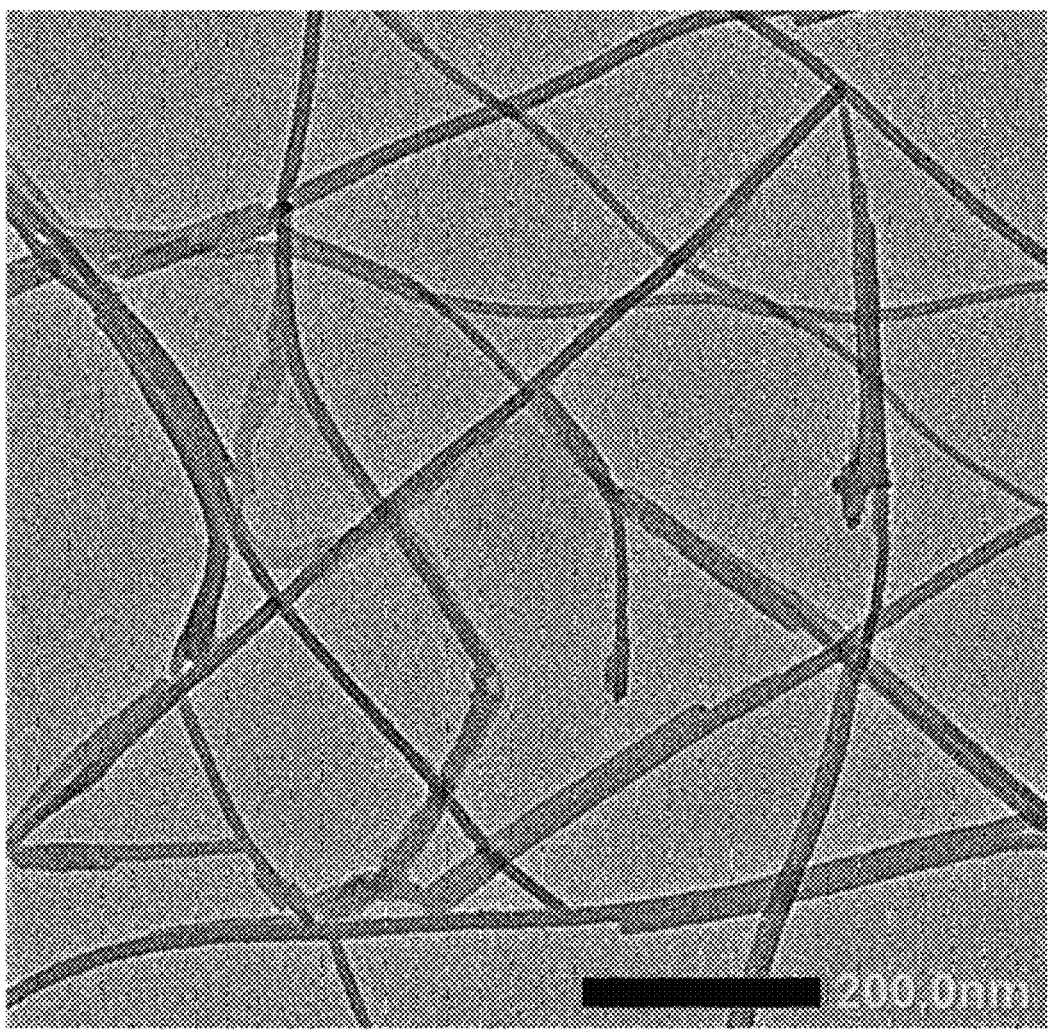
FIG. 8 is a transmission electron microscopic image of a solid content in a phthalocyanine nano-sized substance dispersion liquid (4).

The confirmation of the phthalocyanine nano-sized substance was performed by observing the shape of the solid content of the above dispersion liquid by a transmission electron microscope and observing a crystal structure of the above solid content film by an X-ray diffraction (XRD) measurement. In FIG. 5, a transmission electron microscopic image was shown. From the figure, it was confirmed that the shape of the solid content in the dispersion liquid (1) described above was the nano-sized structure having a major axis and a minor axis in which the minor axis was 100 nm or less. In addition, it was confirmed that the above solid content film showed the peaks at 2θ=6.9, 10.2 and 15.7 by an XRD measurement and had a crystal structure derived from a phthalocyanine α crystal. From the above, it was confirmed that the solid content obtained by the present method of manufacturing was a phthalocyanine nano-sized substance having a major axis and a minor axis in which the minor axis is 100 nm or less.

<Manufacturing of Transistor and Evaluation of Transistor Characteristics (Mobility)>

An n-type silicon substrate was prepared and used as the gate electrode and the gate insulator film was formed composed of silicon oxide by performing a thermal oxidation treatment of the surface layer thereof. On the gate insulator film, the phthalocyanine nano-sized substance dispersion liquid (1) described above was spin-coated and the semiconductor film (the channel) composed of the phthalocyanine nano-sized substance was formed. Next, as to the source drain electrodes composed of a gold thin film, pattern formation was performed by forming a film by vacuum deposition and a transistor (1) was manufactured. Here, the channel length L (the interval between the source electrode and the drain electrode) was set to 75 μm and the channel width W was set to 5.0 mm.

As to the transistor (1) described above, the transistor characteristics were evaluated. The evaluation of the transistor characteristics was performed by applying from 0 to −80 voltage (Vg) with sweeping to the gate electrode and measuring the current (Id) between the source•drain electrodes to which −80 V was applied by using a digital multi-meter (SMU237, manufactured by Keithley Instrument, Inc.). As a result, the mobility was $5 \times 10^{-3}$ and the ON/OFF ratio was $10^4$. Here, the mobility was determined from the slope of $\sqrt{Id}$–Vg by a well-known method. The unit is $cm^2/V \cdot s$. In addition, the ON/OFF ratio was determined by (the maximum value of the absolute value of Id)/(the minimum value of the absolute value of Id).

<Manufacturing of Photoelectric Conversion Element and Evaluation of Photoelectric Conversion Element Characteristics>

150 mg of the phthalocyanine nano-sized substance dispersion liquid (1) described above, 45 mg of PCBM (manufactured by Frontier Carbon Corporation) and 200 mg of o-dichlorobenzene were put into a sample bottle, and irradiated with ultrasonic waves for 30 minutes in an ultrasonic cleaning device (47 kHz), thereby a material for photoelectric conversion element (1) was obtained.

100 nm of an ITO transparent conductive layer which becomes the positive electrode was deposited on the glass substrate by a sputtering method and the patterning was performed to make this into the strip shape of 2 mm width by a photolithographic-etching method. As to the obtained glass substrate with the patterned ITO, after the ultrasonic cleaning was conducted using a neutral detergent, distilled water, acetone and ethanol in this order for 15 minutes three times for each, an UV/ozone treatment was performed for 30 minutes, and spin-coating of a PEDOT:PSS aqueous dispersion liquid (AI4083 (trade name, manufactured by H.C. Starck GmbH)) was performed thereon, thereby the buffer layer 1 having 60 nm thickness, composed of PEDOT:PSS was formed on the ITO transparent electrode layer. After this was dried for 5 minutes on a hot plate which was heated at 100° C., the material for photoelectric conversion layer (1) described above was spin-coated on the above PEDOT:PSS layer and an organic semiconductor layer having 100 nm film thickness, derived from the material for photoelectric conversion layer (1) was formed. Afterward, after "the substrate on which the organic semiconductor layer was formed" described above and a metal mask for evaporation (for the formation of strip pattern of 2 mm width) were arranged in a vacuum evaporation apparatus and the degree of vacuum in the device increased to $5 \times 10^{-4}$ Pa, aluminum which is the negative electrode was evaporated and deposited so as to be the strip pattern of 2 mm width by a resistance heating method (the film thickness: 80 nm). As mentioned above, the photoelectric conversion element (1) of which the area is 2 mm×2 mm (the part in which the ITO layer and the aluminum layer having the strip shape are crossed) was manufactured.

The positive electrode and the negative electrode of the photoelectric conversion element (1) were connected to a digital multi-meter (6241A, trade name (manufactured by ADC CORPORATION)), the current value was measured by sweeping the voltage from −0.1 V to +0.8 V in an ambient atmosphere, under irradiation with pseudo-sunlight of the spectrum shape: AM 1.5 and the irradiation intensity: 100 mW/cm² (a simplified solar simulator XES 151S (trade name, manufactured by SAN-EI ELECTRIC CO., LTD.)) (irradiating from the ITO layer side). At this time, the short-circuit current density (The value of the current density when the applied voltage is 0 V. Hereinafter, $J_{sc}$) was 4.93 mA/cm², the open circuit voltage (The value of the applied voltage when the current density becomes 0. Hereinafter, $V_{oc}$) was 0.56 V, the fill factor (FF) was 0.37, and the photoelectric conversion efficiency (PCE) calculated from these values was 1.01%. Moreover, FF and PCE were calculated by the following expression.

$$FF = JV_{max}/(J_{sc} \times V_{oc})$$

(Here, $JV_{max}$ is a value of the product of the current density and the applied voltage at the point in which the product of the current density and the applied voltage becomes the maximum over the applied voltage between 0 V and the open circuit voltage value.)

$$PCE = [(J_{sc} \times V_{oc} \times FF)/\text{pseudo-sunlight intensity}(100 \text{ mW/cm}^2)] \times 100(\%)$$

Example 2

<Manufacturing of Phthalocyanine Nano-sized Substance and Phthalocyanine Nano-sized Substance Dispersion Liquid>

The phthalocyanine nano-sized substance dispersion liquid (2) was obtained in the same way as in Example (1) except for using sulfamoyl group-substituted phthalocyanine which was obtained in the synthesis example (2) as phthalocyanine having a substituent.

<Manufacturing of Transistor and Evaluation of Transistor Characteristics (Mobility)>

The transistor (2) was obtained in the same way as in Example (1) except for using the phthalocyanine nano-sized substance dispersion liquid (2) described above as a phthalocyanine nano-sized substance dispersion liquid. The evaluation results of characteristics were compiled in Table 1.

Example 3

<Manufacturing of Phthalocyanine Nano-sized Substance and Phthalocyanine Nano-sized Substance Dispersion Liquid>

The phthalocyanine nano-sized substance dispersion liquid (3) was obtained in the same way as Example (1) except using sulfamoyl group substituted phthalocyanine which was obtained in the synthesis example (3) as phthalocyanine having a substituent.

<Manufacturing of Transistor and Evaluation of Transistor Characteristics (Mobility)>

The transistor (3) was obtained in the same way as Example (1) except using the phthalocyanine nano-sized substance dispersion liquid (3) described above as a phthalocyanine nano-sized substance dispersion liquid. The evaluation results of characteristics were compiled in Table 1.

Example 4

<Manufacturing of Phthalocyanine Nano-sized Substance and Phthalocyanine Nano-sized Substance Dispersion Liquid>

The phthalocyanine nano-sized substance dispersion liquid (4) was obtained in the same way as Example (1) except using sulfamoyl group substituted phthalocyanine which was obtained in the synthesis example (4) as phthalocyanine having a substituent.

<Manufacturing of Transistor and Evaluation of Transistor Characteristics (Mobility)>

The transistor (4) was obtained in the same way as Example (1) except using the phthalocyanine nano-sized substance dispersion liquid (4) described above as a phthalocyanine nano-sized substance dispersion liquid. The evaluation results of characteristics were compiled in Table 1.

Example 5

<Manufacturing of Phthalocyanine Nano-sized Substance and Phthalocyanine Nano-sized Substance Dispersion Liquid>

The phthalocyanine nano-sized substance dispersion liquid (5) was obtained in the same way as Example (1) except using sulfamoyl group substituted phthalocyanine which was obtained in the synthesis example (5) as phthalocyanine having a substituent.

<Manufacturing of Transistor and Evaluation of Transistor Characteristics (Mobility)>

The transistor (5) was obtained in the same way as Example (1) except using the phthalocyanine nano-sized substance dispersion liquid (5) described above as a phthalocyanine nano-sized substance dispersion liquid. The evaluation results of characteristics were compiled in Table 1.

Example 6

<Manufacturing of Phthalocyanine Nano-sized Substance and Phthalocyanine Nano-sized Substance Dispersion Liquid>

The phthalocyanine nano-sized substance dispersion liquid (6) was obtained in the same way as Example (1) except using sulfamoyl group substituted phthalocyanine which was obtained in the synthesis example (6) as phthalocyanine having a substituent.

<Manufacturing of Transistor and Evaluation of Transistor Characteristics (Mobility)>

The transistor (6) was obtained in the same way as Example (1) except using the phthalocyanine nano-sized substance dispersion liquid (6) described above as a phthalocyanine nano-sized substance dispersion liquid. The evaluation results of characteristics were compiled in Table 1.

Example 7

<Manufacturing of Phthalocyanine Nano-sized Substance and Phthalocyanine Nano-sized Substance Dispersion Liquid>

The phthalocyanine nano-sized substance dispersion liquid (7) was obtained in the same way as Example (1) except using sulfamoyl group substituted phthalocyanine which was obtained in the synthesis example (7) as phthalocyanine having a substituent.

<Manufacturing of Transistor and Evaluation of Transistor Characteristics (Mobility)>

The transistor (7) was obtained in the same way as Example (1) except using the phthalocyanine nano-sized substance dispersion liquid (7) described above as a phthalocyanine nano-sized substance dispersion liquid. The evaluation results of characteristics were compiled in Table 1.

Example 8

<Manufacturing of Phthalocyanine Nano-sized Substance and Phthalocyanine Nano-sized Substance Dispersion Liquid>

The phthalocyanine nano-sized substance dispersion liquid (8) was obtained in the same way as Example (1) except using sulfamoyl group substituted phthalocyanine which was obtained in the synthesis example (8) as phthalocyanine having a substituent.

<Manufacturing of Transistor and Evaluation of Transistor Characteristics (Mobility)>

The transistor (8) was obtained in the same way as Example (1) except using the phthalocyanine nano-sized substance dispersion liquid (8) described above as a phthalocyanine nano-sized substance dispersion liquid. The evaluation results of characteristics were compiled in Table 1.

Comparison Example 1

Sulfamoyl group substituted phthalocyanine of [Chem. 19] was synthesized by a method described in WO2010/122921.

[Chem. 19]

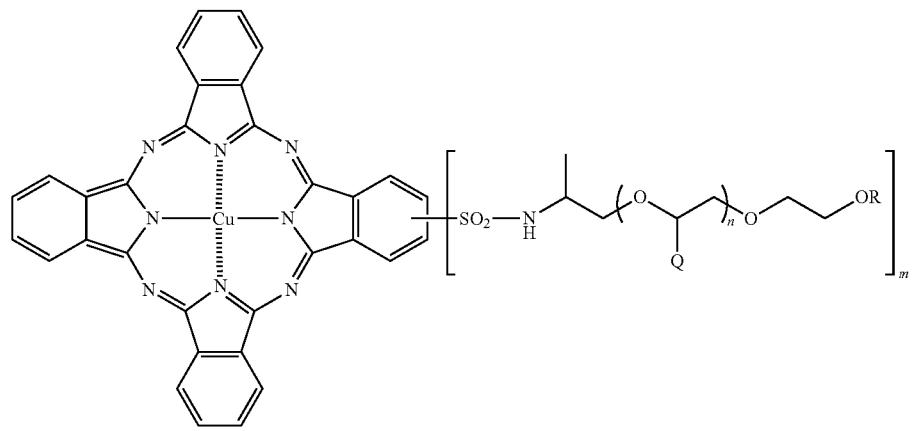

In the compound described above, Q represents a hydrogen atom or a methyl group, propylene oxide/ethylene oxide=29/6 (mol ratio), the average of n=35 and the average of m=1.2.

The phthalocyanine nano-sized substance dispersion liquid (1)' was obtained in the same way as Example (1) except using sulfamoyl group substituted phthalocyanine represented by [Chem. 19] as phthalocyanine having a substituent.

<Manufacturing of Transistor and Evaluation of Transistor Characteristics (Mobility)>

The transistor (1)' was obtained in the same way as Example (1) except using the phthalocyanine nano-sized substance dispersion liquid (1)' described above as a phthalocyanine nano-sized substance dispersion liquid. The evaluation results of characteristics were compiled in Table 1.

Comparison Example 2

The phthalocyanine nano-sized substance dispersion liquid (2)' was obtained in the same way as Example (1) except using a phthalocyanine derivative represented by [Chem. 20] as phthalocyanine having a substituent. As to a preparation of the dispersion liquid, a method described in WO2010/122921 was followed.

[Chem. 20]

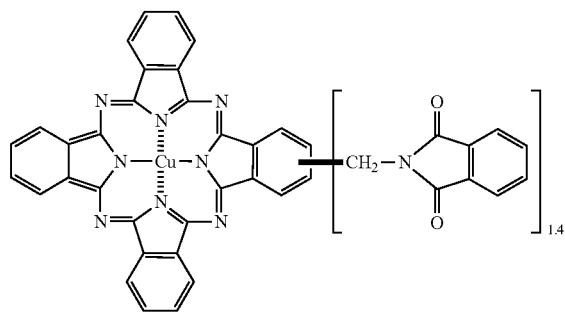

<Manufacturing of Transistor and Evaluation of Transistor Characteristics (Mobility)>

The transistor (2)' was obtained in the same way as Example (1) except using the phthalocyanine nano-sized substance dispersion liquid (2)' described above as a phthalocyanine nano-sized substance dispersion liquid. The evaluation results of characteristics were compiled in Table 1.

TABLE 1

| | Mobility ($cm^2/V \cdot s$) |
|---|---|
| Example 1 | $5 \times 10^{-3}$ |
| Example 2 | $5 \times 10^{-3}$ |
| Example 3 | $5 \times 10^{-3}$ |
| Example 4 | $5 \times 10^{-3}$ |
| Example 5 | $5 \times 10^{-3}$ |
| Example 6 | $5 \times 10^{-3}$ |
| Example 7 | $5 \times 10^{-3}$ |
| Comparison Example 1 | $10^{-4}$ |
| Comparison Example 2 | $10^{-3}$ |

INDUSTRIAL APPLICABILITY

According to a phthalocyanine nano-sized substance of the present invention, since a phthalocyanine derivative having an optimized structure is used for a material configuring a phthalocyanine nano-sized substance, it is possible to create an electronic element (a transistor or the like) of which the characteristics are improved.

REFERENCE SIGNS LIST

1 SUBSTRATE
2 ELECTRODE a
3 PHOTOELECTRIC CONVERSION LAYER
4 ELECTRODE b
5 LAYER CONTAINING PHTHALOCYANINE NANO-SIZED SUBSTANCE OF THE PRESENT INVENTION (IN A CASE ELECTRODE a IS POSITIVE ELECTRODE) OR LAYER CONTAINING ELECTRON ACCEPTING MATERIAL (IN A CASE ELECTRODE a IS NEGATIVE ELECTRODE)
6 LAYER CONTAINING ELECTRON ACCEPTING MATERIAL (IN A CASE ELECTRODE b IS NEGATIVE ELECTRODE) or LAYER CONTAINING PHTHALOCYANINE NANO-SIZED SUBSTANCE OF THE PRESENT INVENTION (IN A CASE ELECTRODE b IS POSITIVE ELECTRODE)
7 SUBSTRATE
8 GATE ELECTRODE
9 GATE INSULATOR FILM
10 SOURCE ELECTRODE
11 DRAIN ELECTRODE
12 SEMICONDUCTOR LAYER CONTAINING PHTHALOCYANINE NANO-SIZED SUBSTANCE OF THE PRESENT INVENTION

The invention claimed is:

1. A phthalocyanine nano-sized substance, comprising:
   unsubstituted phthalocyanine; and
   phthalocyanine having a substituent,
   wherein a shape of the substance has a major axis and a minor axis and the minor axis is 500 nm or less,
   wherein the unsubstituted phthalocyanine is represented by general formula (1) or (2):

[Chem. 1]

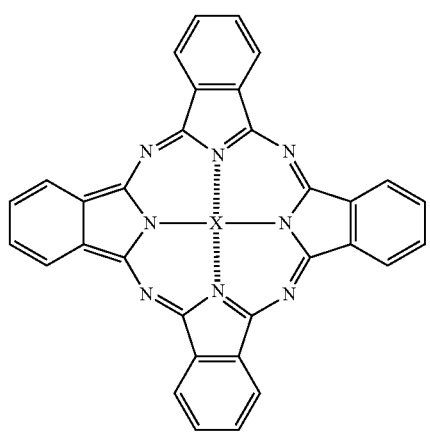

(1)

-continued (2)

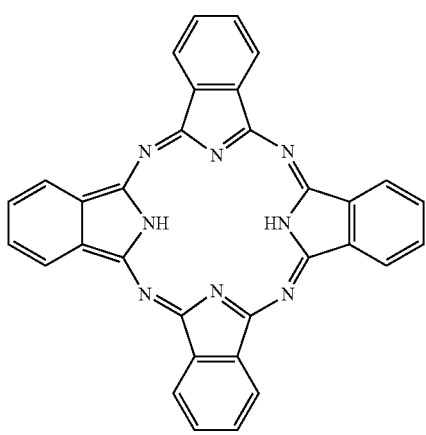

(provided that, in the formulae, X is any one selected from the group composed of a copper atom, a zinc atom, a cobalt atom, a nickel atom, a tin atom, a lead atom, a magnesium atom, an iron atom, a palladium atom, a calcium atom, GeO, TiO, VO and AlCl), and wherein the phthalocyanine having a substituent is represented by general formula (3) or (4):

[Chem. 2]

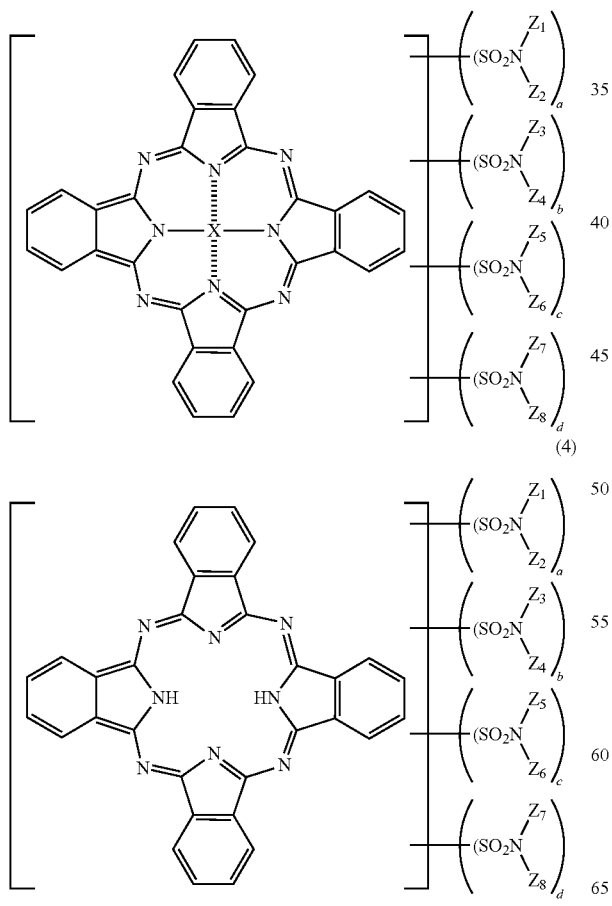

(provided that, in the formulae, X is any one selected from the group composed of a copper atom, a zinc atom, a cobalt atom, a nickel atom, a tin atom, a lead atom, a magnesium atom, an iron atom, a palladium atom, a calcium atom, GeO, TiO, VO and AlCl, each hydrogen atom in a benzene ring of a phthalocyanine skeleton may be substituted with fluorine, chlorine, and bromine, $Z_1$ to $Z_8$ are each independently a hydrogen atom, an acyclic hydrocarbon group having 1 to 30 carbon atoms which may have a substituent, a cyclic hydrocarbon group having 1 to 30 carbon atoms which may have a substituent and a heteroaryl group which may have a substituent, a, b, c and d each independently represent an integer of 0 to 4, but, at least one of those is not 0, and a case where $Z_1$ to $Z_8$ are general formula (5) or (6) and a case where both of them are hydrogen atoms are excluded),

[Chem. 3]

(5)

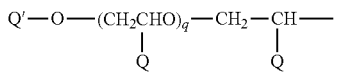

(wherein, q is an integer of 4 to 100, Q is each independently a hydrogen atom or a methyl group, and Q' is an acyclic hydrocarbon group having 1 to 30 carbon atoms),

[Chem. 4]

(6)

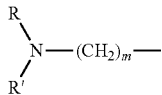

(wherein, m is an integer of 1 to 20, R and R' are each independently an alkyl group having 1 to 20 carbon atoms).

2. The phthalocyanine nano-sized substance according to claim 1, wherein $Z_1$ to $Z_8$ are a group selected from the group composed of an acyclic or a cyclic alkyl group having 1 to 22 carbon atoms, a phenyl group, a thienyl group and the following (7) to (12):

[Chem. 5]

(7)

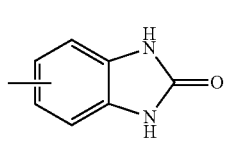

(8)

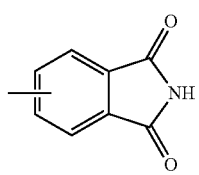

-continued

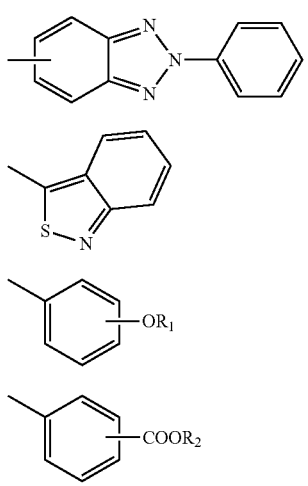

(in the formulae, $R_1$ and $R_2$ represent an alkyl group having 1 to 4 carbon atoms).

3. The phthalocyanine nano-sized substance according to claim 2,
wherein the acyclic or a cyclic alkyl group having 1 to 22 carbon atoms is a methyl group, an ethyl group, a propyl group, an isopropyl group, an n-butyl group, an isobutyl group, a sec-butyl group, a tert-butyl group, a 1-pentyl group, an n-hexyl group, an n-heptyl group, an n-octyl group, an n-nonyl group, an n-decyl group, an n-undecyl group, an n-dodecyl group, an n-tridecyl group, an n-tetradecyl group, an n-pentadecyl group, an n-hexadecyl group, an n-heptadecyl group, an n-octadecyl group, an n-nonadecyl group, an n-docosyl group and a cyclohexyl group.

4. An ink composition, comprising:
the phthalocyanine nano-sized substance according to claim 1; and
an organic solvent, as essential components.

5. An electronic element, comprising:
the phthalocyanine nano-sized substance according to claim 1.

6. A transistor, comprising:
the phthalocyanine nano-sized substance according to claim 1 in a channel.

7. A method of manufacturing the transistor according to claim 6,
wherein the channel is produced by forming a film using an ink composition comprising the phthalocyanine nano-sized substance and an organic solvent as essential components.

8. A photoelectric conversion element having at least a positive electrode and a negative electrode, comprising:
a film containing the phthalocyanine nano-sized substance according to claim 1 between the positive electrode and the negative electrode.

9. A method of manufacturing the photoelectric conversion element according to claim 8, comprising:
a step of forming a film using an ink composition comprising the phthalocyanine nano-sized substance and an organic solvent as essential components between the positive electrode and the negative electrode.

* * * * *